(12) United States Patent
Kosmatopoulos et al.

(10) Patent No.: US 8,465,747 B2
(45) Date of Patent: Jun. 18, 2013

(54) IDENTIFICATION, OPTIMIZATION AND USE OF CRYPTIC HLA-B7 EPITOPES FOR IMMUNOTHERAPY

(75) Inventors: Kostantinos (Kostas) Kosmatopoulos, Paris (FR); Stéphanie Graff-Dubois, Paris (FR); Jeanne Menez-Jamet, Montrouge (FR)

(73) Assignee: Vaxon Biotech, Evry Cedex (FR)

( * ) Notice: Subject to any disclaimer, the term of this patent is extended or adjusted under 35 U.S.C. 154(b) by 720 days.

(21) Appl. No.: 12/373,408

(22) PCT Filed: Jul. 12, 2007

(86) PCT No.: PCT/IB2007/003054
§ 371 (c)(1),
(2), (4) Date: Jul. 9, 2009

(87) PCT Pub. No.: WO2008/010098
PCT Pub. Date: Jan. 24, 2008

(65) Prior Publication Data
US 2011/0256163 A1    Oct. 20, 2011

(30) Foreign Application Priority Data
Jul. 12, 2006  (WO) .................. PCT/IB2006/002937

(51) Int. Cl.
| | |
|---|---|
| *A61K 38/03* | (2006.01) |
| *A61K 38/16* | (2006.01) |
| *C07K 7/00* | (2006.01) |
| *C07K 14/00* | (2006.01) |
| *A61K 39/395* | (2006.01) |

(52) U.S. Cl.
USPC .................... 424/192.1; 424/277.1; 435/810; 530/324; 530/326; 530/328

(58) Field of Classification Search
None
See application file for complete search history.

(56) References Cited

U.S. PATENT DOCUMENTS
6,750,321 B1 * 6/2004 Chen et al. .................... 530/317
2005/0003483 A1   1/2005 Hildebrand et al.

FOREIGN PATENT DOCUMENTS
| | | |
|---|---|---|
| EP | 1 748 067 A | 1/2007 |
| WO | WO99/45954 A1 * | 9/1999 |
| WO | WO00/02581 A1 * | 1/2000 |
| WO | WO 2004/011650 | 2/2004 |
| WO | WO 2007/094924 | 8/2007 |

OTHER PUBLICATIONS

International Search Report and Written Opinion for PCT/IB2007/003054 filed Jul. 12, 2007.
Turcanova V et al: "Sustained CD8+ T-cell immune response to a novel immunodominant HLA-B*0702-associated epitope derived from an Epstein-Barr virus helicase-primase-associated protein"; Journal of Medical Virology, Alan R. Liss, New York, NY, US; vol. 72, No. 4; Apr. 2004; pp. 635-645; XP002408387.
Rammensee Hans-Georg et al: "SYFPEITHI: Database for MHC ligands and peptide motifs"; Immunogenetics, Springer Verlag, Berlin, DE; vol. 50, No. 3-4, Nov. 1999; pp. 213-219; XP002183663.
Pasquetto Valerie et al.: "HLS-A*02021, HLA-A*1101, and HLA-B*0702 transgenic mice recognize numerous poxvirus determinants from a wide variety of viral gene products"; Journal of Immunology; vol. 175, No. 8, Oct. 2005; pp. 5504-5515; XP002419446.
Adotèvi Olivier et al: "Immunogenic HLA-B*0702-restricted epitopes derived from human telomerase reverse transcriptase that elicit antitumor cytotoxic T-cell responses"; Clinical Cancer Research: An Official Journal of the American Association for Cancer Research; vol. 12, No. 10, May 15, 2006; pp. 3158-3167; XP00248969.

* cited by examiner

*Primary Examiner* — Gerald R Ewoldt
*Assistant Examiner* — Marianne Dibrino
(74) *Attorney, Agent, or Firm* — Alston & Bird LLP

(57) ABSTRACT

The invention provides methods for identifying a HLA-B*0702-restricted cryptic epitope in an antigen, as well as methods for increasing the immunogenicity of HLA-B*0702-restricted cryptic epitopes. The HLA-B*0702-restricted cryptic epitopes and their cognate immunogenic epitopes are useful for stimulating an immune reaction against the cryptic epitopes in a subject. Accordingly, the invention further provides pharmaceutical compositions comprising a HLA-B*0702-restricted cryptic epitope or a cognate immunogenic epitope thereof, and vaccination kits comprising such epitopes. The novel materials of the invention are particularly useful for efficiently treating patients having an HLA-B*0702 phenotype.

19 Claims, 6 Drawing Sheets

A

B

IDENTIFICATION, OPTIMIZATION AND USE OF CRYPTIC HLA-B7 EPITOPES FOR IMMUNOTHERAPY

CROSS REFERENCE TO RELATED APPLICATIONS

This application is a national stage application filed under 35 U.S.C. 371 of International Application No. PCT/IB2007/003054, filed Jul. 12, 2007, which claims priority from International Application No. PCT/IB2006/002937, filed Jul. 12, 2006.

FIELD AND BACKGROUND OF THE INVENTION

The present invention relates to the field of peptide immunotherapy. In particular, the invention provides novel methods and materials for efficiently treating patients having an HLA-B*0702 phenotype.

Immunotherapy is a therapeutic approach which is currently the subject of a great deal of interest in the context of the treatment of cancer. The principle thereof is based on immunization with peptides which reproduce T cell epitopes of tumor antigens recognized by cytotoxic T lymphocytes (CTLs) which play a major role in the elimination of tumor cells.

It will be recalled that CTLs do not recognize whole protein antigens, but peptide fragments thereof, generally comprising 8 to 11 amino acids, presented by class I major histocompatibility complex (MHC I) molecules expressed on the surface of cells. The presentation of these peptides is the result of the antigen processing which involves three steps:
- cytosolic degradation of the antigen by a multienzyme complex called proteasome
- translocation of the peptides derived from this degradation in the endoplasmic reticulum (ER) by the TAP transporters
- association of these peptides with the MHC I molecules and exportation of the peptide/MHC I complexes to the cell surface The peptide/MHC I complexes interact with the specific T cell receptor (TCR) on CTL inducing the stimulation and amplification of these CTL which become able to attack target cells expressing the antigen from which the peptide is derived.

During the antigen processing, a peptide selection takes place, which results in a hierarchy of peptides presentation. Peptides that are preferentially presented by the MHC I molecules are called immunodominant while peptides that are weakly presented are called cryptic. Immunodominant peptides exhibit a high affinity for the MHC I and are immunogenic while cryptic peptides exhibit a low affinity for MHC I and are non-immunogenic.

Immunodominant peptides have widely been targeted by tumor vaccines in preclinical and clinical studies with disappointing results (Bowne et al., 1999; Colella et al., 2000; Gross et al., 2004; Hawkins et al., 2000; Naftzger et al., 1996; Overwijk et al., 1998; Vierboom et al., 1997; Weber et al., 1998).

Tumor antigens are frequently self proteins over-expressed by tumors and expressed at lower levels by normal cells and tissues. Immune system is unable to react against these self antigens because of the self tolerance process. Self-tolerance concerns mainly the immunodominant peptides (Cibotti et al., 1992; Gross et al., 2004; Hernandez et al., 2000; Theobald et al., 1997) thus explaining the incapacity of these peptides to induce a tumor immunity.

Cryptic peptides are much less involved in self tolerance process (Anderton et al., 2002; Boisgérault et al., 2000; Cibotti et al., 1992; Friedman et al., 2004; Gross et al., 2004; Moudgil et al., 1999; Overwijk et al., 2003; Sinha et al., 2004) and can therefore induce an efficient tumor immunity providing their immunogenicity is enhanced (Disis et al., 2002; Dyall et al., 1998; Engelhorn et al., 2006; Gross et al., 2004; Grossmann et al., 2001; Lally et al., 2001; Moudgil and Sercarz, 1994a; Moudgil and Sercarz, 1994b; Palomba et al., 2005).

The usual strategy for enhancing the immunogenicity of cryptic peptides, that because of their low MHC I affinity are non-immunogenic, consists in increasing their affinity for the MHC I molecules via amino acids substitutions. Peptide affinity for MHC I molecules mainly depends on the presence at well defined positions (primary anchor positions) of residues called "primary anchor residues". These residues are MHC I allele specific. The presence of primary anchor residues although often necessary is not sufficient to ensure a high MHC I affinity. It has been shown that residues located outside the primary anchor positions (secondary anchor residues) may exert a favourable or unfavourable effect on the affinity of the peptide for the MHC I (Parker et al., 1994; Rammensee H et al., 1999). The presence of these secondary anchor residues makes it possible to explain the existence, within the peptides having the primary anchor motifs, of a great variability in the binding affinity.

Amino acids substitutions aiming at enhancing affinity for MHC I molecule should preserve the antigenicity of such optimized peptides. CTL generated by optimized peptides should cross-react with the corresponding native peptides.

Many teams have succeeded in further enhancing immunogenicity of already immunogenic peptides by increasing their affinity for HLA-A*0201 (Bakker et al., 1997; Parkhurst et al., 1996; Sarobe et al., 1998; Valmori et al., 1998). The inventors have previously described a general strategy to enhance affinity and immunogenicity of HLA-A*0201 restricted cryptic peptides (Scardino et al., 2002; Tourdot et al., 2000).

HLA-B*0702 is a frequently expressed molecule (25% of the population). Identification and optimization of HLA-B*0702 restricted tumor cryptic peptides should therefore be necessary in order to develop efficient cancer vaccines for HLA-B*0702 expressing patients.

Few tumor peptides presented by HLA-B*0702 have been described to date. Two peptides derived from the CEA ($CEA_{632}$) (Lu et al. 2000) and TERT ($TERT_{1123}$) (Cortez-Gonzales et al. 2006) antigens have been identified; these peptides exhibited a strong binding affinity for HLA-B*0702 and were immunogenic both in HLA-B*0702 transgenic mice and in vitro tests with human cells. These experimental results show that these peptides are immunodominant peptides.

Two additional peptides derived from MAGE-A 1 ($MAGE-A1_{289}$) (Luiten et al., 2000) and RU2 (a new antigen expressed by renal cell carcinoma) (Van den Eynde et al. 1999) have been identified to be targets of HLA-B*0702 CTL that had been isolated from cancer patients. Although there is no information about the HLA-B*0702 affinity of these two peptides, we can consider them immunodominant because CTL developed in cancer patients are always directed against immunodominant peptides.

SUMMARY OF THE INVENTION

As described in the experimental part below, the inventors have now found a general strategy to enhance affinity and immunogenicity of a HLA-B*0702 restricted cryptic peptide.

In a first aspect, the present invention provides a method for increasing the immunogenicity of a HLA-B*0702-restricted cryptic epitope, comprising a step of substituting the N-terminal residue of said epitope with an alanine (A), or substituting the C-terminal residue of said epitope with a leucine (L).

In what follows, the phrases "HLA-B*0702-restricted cryptic epitope" is used to designate a peptide, having 8 to 11 amino acids, more preferably 9 or 10 amino acids, which exhibits a low affinity for HLA-B*0702, is non immunogenic and has the sequence $X_1PX_3X_4X_5X_6X_7X_8X_9X_{10}X_{11}$ (SEQ ID NO: 58), wherein P is for proline, $X_3$ is R (arginine) or K (lysine) or H (histidine) or M (methionine), $X_1$ and $X_4$ to $X_7$ are independently any amino acid, $X_8$ to $X_{10}$ are independently any amino acid or none, and the C-terminal amino acid $X_{11}$ is any amino acid with the proviso that if the N-terminal amino acid $X_1$ is A (alanine) then $X_{11}$ is neither L (leucine) nor A, nor I (isoleucine), nor V (valine), and nor M, and if X1 is an amino acid other than A then $X_{11}$ is L or A or I or V or M.

In the present text, the term "peptide" designates not only molecules in which amino acid residues are joined by peptide (—CO—NH—) linkages, but also synthetic pseudopeptides or peptidomimetics in which the peptide bond is modified, especially to become more resistant to proteolysis, and provided their immunogenicity is not impaired by this modification.

In the present text, the amino acid residues are designated by their one letter codes.

As used herein, the word "substituting" is to be understood as obtaining a peptide, the sequence of which is derived from the sequence of said HLA-B*0702-restricted cryptic epitope by the mentioned substitution, when the amino acid sequence of said cryptic epitope does not contain the appropriate amino acid, whatever the technical method used to obtain said peptide. For example, the peptide can be produced by artificial peptide synthesis or by recombinant expression.

The affinity of a peptide for HLA-B*0702 can be determined by methods known in the art, for instance by the assay described by Rohrlich et al., 2003. Results are expressed as relative affinity (RA) when compared to a reference peptide. Following this method a peptide is said to have a low affinity for HLA-B*0702 when RA is greater than 10. Peptides with RA greater than 10 are therefore considered to be cryptic peptides (or epitopes).

As used herein, the term "non immunogenic" refers to a peptide unable to initiate a HLA-B*0702-restricted CTL immune response when administered to a subject expressing HLA-B*0702 (including a HLA-B*0702 transgenic animal).

In another embodiment, the immunogenicity of a HLA-B*0702-restricted cryptic epitope in which the second and third amino acid residues are PR or PK or PH or PM and the last residue is L or A or I or V or M, can be increased by substituting its first amino-acid by an A (alanine). Indeed, when the sequence of the selected HLA-B*0702-restricted cryptic epitope is $X_1PX_3X_4X_5X_6X_7X_8X_9 X_{10}X_{11}$ (SEQ ID NO: 59), wherein the N-terminal amino acid $X_1$ is any amino acid but A, $X_3$ is R or K or H or M, the C-terminal amino acid $X_{11}$ is L or A or I or V or M, $X_4$ to $X_7$ are independently any amino acid, and $X_8$ to $X_{10}$ are independently any amino acid or none, the substitution of $X_1$ by A is sufficient to increase its immunogenicity.

In yet another embodiment, the immunogenicity of HLA-B*0702-restricted cryptic epitopes in which the three first amino acid residues are $APX_3$ (wherein $X_3$ is R or K or H or M) can be increased by substituting its last amino-acid by a L (or by adding a leucine at its C-terminus, provided the amino acid sequence of said epitope after having added the leucine is not longer than 11 amino acids). Indeed, when the sequence of the selected HLA-B*0702-restricted cryptic epitope is $APX_3X_4X_5X_6X_7X_8X_9X_{10}X_{11}$ (SEQ ID NO: 60), wherein $X_3$ is R or K or H or M, $X_4$ to $X_7$ are independently any amino acid, $X_8$ to $X_{10}$ are independently any amino acid or none, and the C-terminal amino acid $X_{11}$ is an amino acid other than L or A or I or V or M, the substitution of $X_{11}$ by L is sufficient to increase its immunogenicity.

In what follows, the expression "optimized peptide" designates an immunogenic peptide derived from a HLA-B*0702-restricted cryptic epitope by the above methods, and having the general sequence $APX_3X_4X_5X_6X_7X_8X_9X_{10}X_{11}$ (SEQ ID No: 61), wherein $X_3$ is R or K or H or M, $X_4$ to $X_7$ are independently any amino acid, $X_8$ to $X_{10}$ are independently any amino acid or none, and the C-terminal amino acid $X_{11}$ is L or A or I or V or M.

The inventors have identified a number of HLA-B*0702-restricted cryptic epitopes, some of them are disclosed in Table I below. Accordingly, another aspect of the present invention is a cryptic HLA-B*0702-restricted epitope, selected amongst the peptides of SEQ ID NOs: 1 to 4, disclosed in Table I.

TABLE I

Selected cryptic HLA-B*0702 restricted peptides

| Antigen | Peptide | SEQ ID NO: |
|---------|---------|------------|
| $TERT_{444}$ | DPRRLVQLL | 1 |
| HER-2/neu | APRSPLAPS | 2 |
|  | SPKANKEIL | 3 |
|  | GPKHSDCLA | 4 |

Examples of immunogenic HLA-B*0702-restricted epitopes obtained according to the present invention are those derived from a cryptic HLA-B*0702-restricted epitope SEQ ID NOs 1, 3, 4, by substitution of their N-terminal amino-acid with an A (alanine) and those derived from the cryptic HLA-B*0702-restricted epitope SEQ ID NOs: 2 by substitution of their C-terminal amino-acid with a L (leucine).

Therefore, the present invention also pertains to optimized peptides derived from the cryptic peptides of SEQ ID NOs: 1 to 4, by a method according to the invention. Preferred examples of optimized peptides are APRSPLAPL (SEQ ID NO: 6), APKANKEIL (SEQ ID NO: 7), APKHSDCLA (SEQ ID NO: 8) and APRRLVQLL (SEQ ID NO: 5).

The invention also concerns a chimeric polypeptide, comprising two, three or more HLA-B*0702-restricted cryptic epitopes or two, three or more immunogenic HLA-B*0702-restricted epitopes as described above. In a chimeric polypeptide according to the invention, the epitopes can be different from each other, or the same epitope can be repeated several times (two, three or more times). The skilled artisan can chose any known technique to produce such polypeptides. For example, the polypeptide can be obtained by chemical synthesis, or by using the technology of genetic engineering.

Another object of the present invention is an isolated nucleic acid molecule designed to cause the expression of a cryptic HLA-B*0702-restricted epitope or an immunogenic epitope or a chimeric polypeptide as above-described. By "designed to cause the expression of" a peptide is herein meant that said peptide is expressed as such, isolated from the whole antigen from which its sequence has been selected (and, in appropriate cases, optimized as above-described), when the nucleic acid is introduced in an appropriate cell. The encoding region for the epitope or chimeric polypeptide will typically be situated in the polynucleotide under control of a suitable promoter. Bacterial promoters will be preferred for expression in bacteria, which can produce the polypeptide either in vitro, or, in particular circumstances, in vivo. An example of bacterium that can be used to produce a peptide or polypeptide according to the invention, directly in vivo, is *Listeria monocytogenes*, which is a facultative intracellular bacterium that enters professional antigen-presenting cells by active phagocytosis (Paterson and Maciag, 2005). Alternatively, a nucleic acid according to the invention can be administered directly, using an appropriate vector. In this case, a tissue-specific, a strong constitutive, or an endogenous promoter can be used to control the peptide expression. Suitable vector systems include naked DNA plasmids, liposomal compositions to enhance delivery, and viral vectors that cause transient expression. Exemplary are adenovirus or vaccinia virus vectors and vectors of the herpes family, especially in a non-replicative form.

Another embodiment of the present invention is a pharmaceutical composition comprising at least, as an active principle, a HLA-B*0702-restricted cryptic epitope as above-described, or an immunogenic epitope polypeptide derived therefrom as mentioned above, or a chimeric polypeptide according to the invention, or a nucleic acid encoding any of these, and/or a vector carrying said nucleic acid. Formulation of pharmaceutical compositions will accord with contemporary standards and techniques. Medicines intended for human administration will be prepared in adequately sterile conditions, in which the active ingredient(s) are combined with an isotonic solution or other pharmaceutical carrier appropriate for the recommended therapeutic use. Suitable formulations and techniques are generally described in the latest edition of Remington's Pharmaceutical Sciences (Maack Publishing Co, Easton Pa.).

In particular, a HLA-B*0702-restricted cryptic epitope, or an immunogenic epitope polypeptide derived therefrom, or a chimeric polypeptide carrying several such immunogenic or cryptic epitopes, or a nucleic acid encoding any of these, included or not in a vector, can be used for the preparation of a composition for preventive or curative immunotherapy, especially, for antiviral or anti-cancer immunotherapy.

In a particular embodiment, a pharmaceutical composition according to the invention is a vaccine. In this latter case, the compositions of this invention can be combined with an adjuvant to potentiate the immune response. Classic adjuvants include oil emulsions, like Incomplete Freund's Adjuvant, and adherent surfaces such as alum. Adjuvants that recruit and activate dendritic cells particularly via TLR (such as bacterial DNA or bacterial membrane derived proteins) or help to elicit cytotoxic T cells are especially useful. Other factors that otherwise boost the immune response or promote apoptosis or elimination of cancer cells can also be included in the composition.

Multiple doses and/or different combinations of the immunogenic compositions of this invention can be packaged for distribution separately or together. Each composition or set of compositions, such as the kits of parts described below, can be accompanied with written instructions (in the form of promotional material or a package insert) regarding the use of the composition or combination in eliciting an immune response and/or the treatment of cancer.

In a previous patent application (PCT/EP2006/005325), the Applicant has described a vaccination protocol which enables the initiation and maintenance of a T cell response targeting cryptic epitopes. The results reported in PCT/EP2006/005325 demonstrate that injection of a native peptide corresponding to a cryptic epitope, following vaccination with its cognate optimized peptide, can maintain the immune response initiated by said optimized peptide.

According to the invention, a HLA-B*0702-restricted cryptic epitope can hence be used for the preparation of a medicinal composition for maintaining the CTL immune response initiated by its cognate optimized peptide. An immunogenic peptide having an optimized HLA-B*0702-restricted epitope sequence derived from a HLA-B*0702-restricted cryptic epitope can also be used, for the preparation of a medicinal composition for initiating a CTL immune response against said HLA-B*0702-restricted cryptic epitope. The present invention also encompasses a method for vaccinating a patient against a tumoral or viral antigen, wherein said method comprises a first step of vaccination with an optimized peptide cognate to a native HLA-B*0702-restricted cryptic epitope of said antigen, followed by a second step of vaccination with said native peptide. In such a method, the first step and/or the second step can be performed by using a chimeric polypeptide comprising two, three or more optimized or cryptic peptides as above-described, instead of single-epitope peptides.

The invention also pertains to a kit of parts comprising, in separate formulations, a first peptide having the sequence of a HLA-B*0702-restricted cryptic epitope, and a second peptide corresponding to its cognate HLA-B*0702-restricted immunogenic epitope. Examples of peptides which can be part of a kit according to the invention are the peptides of SEQ ID NOs: 1 to 4, which can constitute the first peptide, the second peptide being then derived from said first peptide by a method for increasing its immunogenicity, as described above.

Other kits of parts according to the invention comprise at least a chimeric polypeptide. Several variants of such kits are contemplated: in a first embodiment, the kit comprises, in separate formulations, a first chimeric polypeptide comprising two, three or more HLA-B*0702-restricted cryptic epitopes, and a second chimeric polypeptide corresponding to its cognate HLA-B*0702-restricted immunogenic chimeric polypeptide (which means that it comprises optimized HLA-B*0702-restricted immunogenic epitopes cognate to the cryptic epitopes comprised in the first chimeric polypeptide). In a second embodiment, the kit comprises a first chimeric polypeptide comprising two, three or more HLA-B*0702-restricted cryptic epitopes and, in one or several other separate formulations, peptides corresponding to the optimized HLA-B*0702-restricted immunogenic epitopes cognate to the cryptic epitopes comprised in the first chimeric polypeptide. In a third embodiment, the kit comprises two, three or more peptides corresponding to distinct HLA-B*0702-restricted cryptic epitopes, wherein said peptides are either mixed in one single formulation, or separated in several formulations and, in a separate formulation, a chimeric polypeptide comprising the optimized HLA-B*0702-restricted immunogenic epitopes cognate to said cryptic peptides.

In the following description of the kits according to the invention, mention will be made only of the peptides (native or optimized), it being understood that chimeric polypeptides (comprising native cryptic epitopes or optimized epitopes) can be enclosed in the kits instead of single-epitope peptides.

In a particular embodiment of the invention, the kit is a vaccination kit, wherein said first (native) and second (cognate optimized) peptides are in separate vaccination doses. In a preferred embodiment, the vaccination kit comprises 2 or 3 doses of optimized peptide, and 3, 4, 5 or 6 doses of native peptide. A particular vaccination kit according to the invention is adapted for the first vaccination sequence of 6 injections, and comprises 2 or 3 doses of optimized peptide, and 4 or 3 doses of native peptide. In case of long-lasting diseases, it is preferable to maintain the level of immunity obtained after this primo-vaccination, by regular recalls. This can be done, for example, by injections performed every 1.5 to 6 months. Therefore, complementary kits, comprising at least 2 doses, and up to 40 or 50 doses of native peptide, are also part of the present invention. Alternatively, the vaccination kit can comprise 2 to 3 doses of optimized peptide, and 3 to 40 or up to 50 doses of native peptide. Of course, said native and optimized peptides present in the kit are as described above.

Each dose comprises between 0.5 and 10 mg of peptide, preferably from 1 to 5 mg, or between 1 and 20 mg of polypeptide. In a preferred embodiment, each dose is formulated for subcutaneous injection. For example, each dose can be formulated in 0.3 to 1.5 ml of an emulsion of aqueous solution emulsified with Montanide, used as an adjuvant. The skilled artisan can choose any other adjuvant(s) in place of (or in addition to) Montanide. In a particular embodiment, the doses are in the form of an aqueous solution. Alternatively, the doses can be in the form of a lyophilized peptide, for extemporaneous preparation of the liquid solution to be injected. Other possible components of said kits are one or several adjuvants, to be added to the peptide compositions before administration, and a notice describing how to use said kits.

BRIEF DESCRIPTION OF THE DRAWINGS

The invention is further illustrated by the following figures and examples.

EXAMPLES

Figure 1:
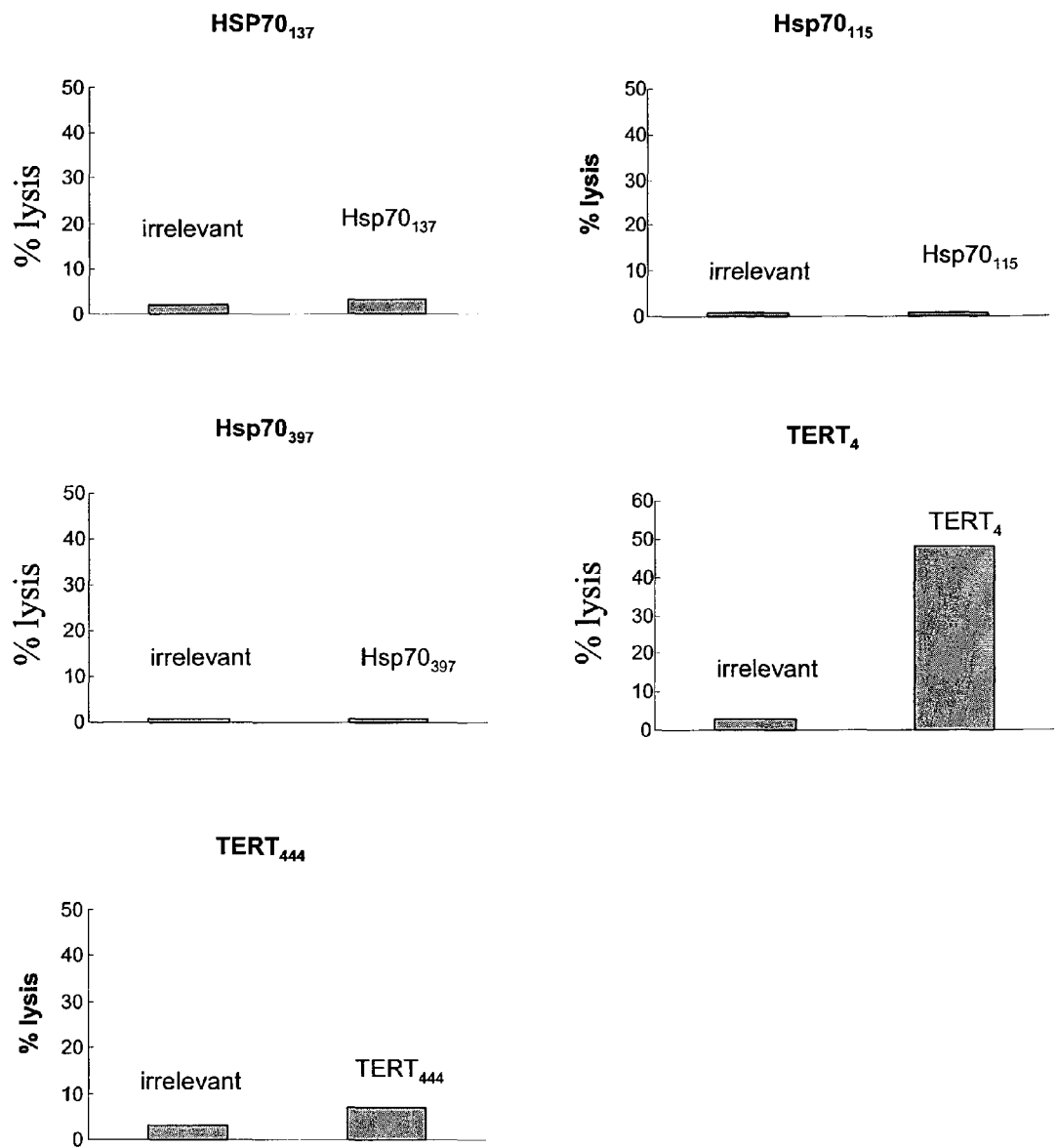
FIG. 1: Immunogenicity of HLA-B*0702 restricted peptides. CTL were tested against RMA-B7 targets loaded with peptide as indicated.

The examples have been performed using the following materials and methods:

Transgenic Mice. The HLA-B7 H-2 class-I knockout mice were previously described (Rohrlich et al., 2003).

Cells. HLA-B*0702 transfected murine RMA-B7 and human T2-B7 cells were previously described (Rohrlich et al., 2003). COS-7 and WEHI-164 clone 13 cells were provided by F. Jotereau (INSERM 463, Nantes, France). The HLA-B*0702 positive SK-MES-1 (lung cancer), HBL-100 (breast cancer), and the HLA-B*0702 negative SW-480 (colon cancer) and HSS (myeloma) cell lines were used as targets of human CTL. All cell lines were grown in FCS 10% supplemented RPMI1640 culture medium.

Peptides and Plasmids. Peptides were synthesized by Epytop (Nîmes, France). HLA-B*0702 plasmid was provided by Dr. Lemonnier (Institut Pasteur, Paris, France) (Rohrlich et al., 2003) and TERT plasmid was provided by Dr Weinberg (MIT, Boston, Mass.) (Meyerson et al, 1997).

Measurement of Peptide Relative Affinity to HLA-B*0702. The protocol used has been described previously (Rohrlich et al., 2003). Briefly, T2-B7 cells were incubated at 37° C. for 16 hours with peptides concentrations ranging from 100 µM to 0.1 µM, and then stained with ME-1 monoclonal antibody (mAb) to quantify the surface expression of HLA-B*0702. For each peptide concentration, the HLA-B*0702 specific staining was calculated as the percentage of staining obtained with 100 µM of the reference peptide CMV$_{265-274}$ (R10V; RPHERNGFTV, SEQ ID NO: 9). The relative affinity (RA) was determined as: RA=(Concentration of each peptide that induces 20% of HLA-B*0702-expression/Concentration of the reference peptide that induces 20% of HLA-B*0702 expression).

CTL Induction in vivo in HLA-B*0702 Transgenic Mice. Mice were injected subcutaneously with 100 µg of peptide emulsified in Incomplete Freund's Adjuvant (IFA) in the presence of 150 µg of the I-A$^b$ restricted HBVcore$_{128}$ T helper epitope (TPPAYRPPNAPIL, SEQ ID NO: 10). After 11 days, 5×10$^7$ spleen cells were stimulated in vitro with peptide (10 µM). On day 6 of culture, the bulk responder populations were tested for specific cytotoxicity.

Peptide Processing Assay on COS-7 Transfected Cells. 2.2×10$^4$ simian COS-7 cells were plated in flat-bottomed 96-well plates in DMEM+10% FCS, in triplicate for each condition. Eighteen hours later, cells were transfected with 100 ng of each DNA plasmid with DEAE Dextran. After 4 hours, PBS+10% DMSO was added for 2 minutes. Transfected COS cells were incubated in DMEM+10% FCS during 40 hours and then used to stimulate murine CTL in a TNFα secretion assay.

TNFα Secretion Assay. Transfected COS-7 cells at day 4 were suspended in 50 µl of RPMI+10% FCS and used as stimulating cells. 5×10$^4$ murine T cells were then added in 50 µl RPMI 10% FCS and incubated for 6 hours. Each condition was tested in triplicate. 50 µl of the supernatant was collected to measure TNFα. Standard dilutions were prepared in 50 µl with final doses of TNFα ranging from 104 to 0 pg/ml. On both the supernatants and the standard dilutions, 3×10$^4$ TNFα sensitive WEHI-164c13 cells in 50 μl were added. They were incubated for 16 h at 37° C. Inhibition of cell proliferation was evaluated by the MTT colorimetric method (Espevik and Nissen-Meyer, 1986).

Generation of CTL from human PBMC. PBMC were collected by leukapheresis from healthy HLA-B*0702 volunteers. Dendritic cells (DC) were produced from adherent cells cultured for seven days ($2\times10^6$ cells/ml) in the presence of 500 IU/ml GM-CSF and 500 IU/ml IL-4 (R&D Systems, Minneapolis, Minn.) in complete medium (RPMI-1640 supplemented with 10% heat inactivated human AB serum, 2 μM L-Glutamine and antibiotics). On day seven, DC were pulsed with 10 μM peptides for 2 hrs; maturation agents Poly I:C (Sigma, Oakville, Canada) at 100 ng/ml and anti-CD40 mAb (clone G28-5, ATCC, Manassas, Va.) at 2 μg/ml were added in the culture and DCs were incubated at 37° C. overnight or up to 48 hours. Mature DC were then irradiated (3500 rads). CD8+ cells were purified by positive selection with CD8 MicroBeads (Miltenyi Biotec, Auburn, Calif.) according to the manufacturer's instructions. $2\times10^5$ CD8$^+$ cells+$6\times10^4$ CD8$^-$ cells were stimulated with $2\times10^4$ peptide pulsed DC in complete culture medium supplemented with 1000 IU/ml IL-6 and 5 IU/ml IL-12 (R&D Systems, Minneapolis, Minn.) in round-bottomed 96 well plates. From day seven, cultures were weekly restimulated with peptide-loaded DC in the presence of 20 IU/ml IL-2 (Proleukin, Chiron Corp., Emeryville, Calif.) and 10 ng/ml IL-7 (R&D Systems, Minneapolis, Minn.). After the third in vitro restimulation, bulk cell cultures were tested for cytotoxicity (TERT$_4$) or for IFNγ intracellular staining (TERT$_{444A1}$).

Cytotoxic assay. Targets were labelled with 100 μCi of Cr$^{51}$ for 60 min, plated in 96-well V-bottomed plates ($3\times10^3$ cell/well in 100 μL of RPMI 1640 medium) and, when necessary, pulsed with peptides (1 μM) at 37° C. for 2 hours. Effectors were then added in the wells and incubated at 37° C. for 4 hours. Percentage of specific lysis was determined as: % Lysis=(Experimental Release−Spontaneous Release)/(Maximal Release−Spontaneous Release)×100.

IFNγ intracellular staining. T cells ($10^5$) were incubated with $2\times10^5$ T2 cells loaded with stimulating peptide in the presence of 20 μg/ml Brefeldin-A (Sigma, Oakville, Canada). Six hours later they were washed, stained with r-phycoerythrin-conjugated anti-CD8 antibody (Caltag Laboratories, Burlingame, Calif., USA) in PBS for 25 min at 4° C., washed again, and fixed with 4% PFA. The cells were then permeabilized with PBS, 0.5% BSA, 0.2% saponin (Sigma, Oakville, Canada), and labeled with an allophycocyanin-conjugated anti-IFNγ mAb (PharMingen, Mississauga, Canada) for 25 min at 4° C. before analysis with a FACSCalibur® flow cytometer.

Example 1

Affinity of Peptides

Eight peptides with the HLA-B*0702 specific anchor motifs, i.e. P2 and preferentially LN at C-terminal position (Sidney et al., 1996) belonging to Hsp70 (Hsp70$_{115}$, Hsp70$_{137}$, Hsp70$_{397}$), TERT (TERT$_4$ and TERT$_{444}$), and MAGE-A (MAGE-A$_{121.1}$, MAGE-A$_{121.2}$ and MAGE-A$_{121.4}$) antigens were tested for binding to the HLA-B*0702 molecule. Only TERT$_4$ bound to HLA-B*0702 with a high affinity, the remaining seven peptides were very weak or non binders (Table II). This demonstrates that the presence of anchor motifs is not sufficient to ensure a high binding affinity to HLA-B*0702. Given their low affinity, peptides Hsp70$_{115}$, Hsp70$_{137}$, Hsp70$_{397}$, TERT$_{444}$, MAGE-A$_{121.1}$, MAGE-A$_{121.2}$, MAGE-A$_{121.4}$, are considered cryptic peptides.

TABLE II

HLA-B*0702 affinity of peptides

| | peptide | sequence | RA | SEQ ID No |
|---|---|---|---|---|
| 1 | Hsp70 115 | YPEEISSMVL | >10 | 11 |
| | Hsp70 115A1 | APEEISSMVL | >10 | 12 |
| 2 | Hsp70 137(10) | YPVTNAVITV | >10 | 13 |
| 3 | Hsp70 397 | APLSLGLET | >10 | 14 |
| 4 | TERT4 | APRCRAVRSL | 0.74 | 15 |
| 5 | TERT444 | DPRRLVQLL | >10 | 1 |
| | TERT 444A1 | APRRLVQLL | 1.4 | 5 |
| 6 | MAGE-A121.1 | EPVTKAEML | >10 | 16 |
| | MAGE-121.1 A1 | APVTKAEML | >10 | 17 |
| 7 | MAGE-A121.2 | EPFTKAEML | >10 | 18 |
| 8 | MAGE-A121.4 | EPITKAEIL | >10 | 19 |

Example 2

Immunogenicity of Selected Peptides

The low affinity Hsp$_{137}$, Hsp$_{115}$, Hsp$_{397}$, TERT$_{444}$ and the high affinity TERT$_4$ peptides have been tested for their capacity to induce a specific CTL immune response in HLA-B*0702 transgenic mice. Only the high affinity TERT$_4$ was immunogenic confirming that immunogenicity of peptides is strongly related to their affinity for HLA (FIG. 1).

Example 3

Enhancement of affinity of Low Affinity Peptides

Since all these cryptic peptides had favourable primary anchor motifs, enhancement of their affinity is a prerequisite for them to be immunogenic. It required the identification of unfavourable secondary anchor motifs and their substitution with favourable motifs. These substitutions should however preserve the conformation of the peptide segment that interacts with the TCR (position 4 to position 8). The interest was, therefore, focused on secondary anchor positions 1 and 3: aliphatic amino acids are favourable motifs at position 1 (Sidney, Southwood et al., 1996). However, peptides Hsp70$_{115}$ and Hsp70$_{137}$ that have a Y (tyrosine) at position 1 are non binders. Moreover, the substitution of the amino acid at position 1 by an A (alanine) that is also favourable at this position. (Parker et al, 1994) enhances the affinity of the TERT$_{444}$ but not of the Hsp70$_{115}$ and the MAGE-A$_{121.1}$ peptides (Table II). This indicates that the presence of favourable amino acids at position 1 and anchor positions 2 and 9/10 cannot ensure by itself a high binding affinity of all peptides. In the other hand, positively charged peptides (R/H/K) have been described to be favourable at position 3 (Sidney et al., 1996) and ten out of 26 identified tumor and HIV derived immunogenic peptides have an R/K/H at position 3 (Table III).

TABLE III

Tumor and HIV derived HLA-B*0702 restricted epitopes

| Antigen | sequence | SEQ ID NO: | reference |
|---|---|---|---|
| NY-ESO-1 | APRGVRMAV | 20 | Slager et al, 2004 |
| ICE | SPRWWPTCL | 21 | Ronsin et al., 1999 |
| RAGE-1 | SPSSNRIRNT | 22 | Gaugler et al., 1996 |
| RU2AS | LPRWPPPQL | 23 | Van Den Eynde et al., 1999 |
| RBAF500 | RPHVPESAF | 24 | Lennerz et al., 2005 |
| SSX2 fusion protein | QPRYGYDQIM | 25 | Worley et al, 2001 |
| HIVp17 | RPGGKKRYKL | 26 | HIV Molecular Immunology Database (Operated by Los Alamos National Security, LLC, for the U.S. Department of Energy's National Nuclear Security Administration) |
| HIVp24 | SPRTLNAWV | 27 | |
| HIVp24 | HPVHAGPIA | 28 | |
| HIVp24 | PPIPVGEIY | 29 | |
| HIVp24 | GPGHKARVL | 30 | |
| HIV-RT | SPIETVPVKL | 31 | |
| HIV-RT | GPKVKQWPLT | 32 | |
| HIV-RT | SPAIFQSSM | 33 | |
| HIV-RT | IPLTEEAEL | 34 | |
| HIV-RT | QPDKSESELV | 35 | |
| HIV-Vif | HPRISSEVHI | 36 | |
| HIV-Vif | KPPLPSVKKL | 37 | |
| HIV-Vif | FPRTWLHGL | 38 | |
| HIVgp160 | KPCVKLTPLC | 39 | |
| HIVgp160 | KVVSTQLLL | 40 | |
| HIVgp160 | RPWNNTRKSI | 41 | |
| HIVgp160 | IPRRIRQGL | 42 | |
| HIVnef | FPVTPQVPL | 43 | |
| HIVnef | TPQVPLRPM | 44 | |

According to all these observations, peptides with the sequence $APX_3X_4X_5X_6X_7X_8X_9X_{10}X_{11}$ (SEQ ID No. 61) should have a high affinity for HLA-B*0702. This is confirmed by results shown in Table IV. All eighteen peptides with the above cited sequence had a high affinity and/or were immunogenic in HLA-B*0702 transgenic mice.

TABLE IV

Affinity and immunogenicity of $APX_3X_4X_5X_6X_7X_8X_9X_{10}X_{11}$ HLA-B*0702 restricted peptides.

| Sequence | SEQ ID NOs | RA | Immunogenicity |
|---|---|---|---|
| APRRLVQLL | 5 | + | + |
| APRSPLAPL | 6 | ++ | + |
| APKANKEIL | 7 | ND | + |
| APKHSDCLA | 8 | ND | + |
| APRCRAVRSL | 15 | + | + |
| APRMHCAVDL | 45 | ++ | + |
| APRVSIRLPL | 46 | ++ | ND |
| APREYVNAL | 47 | + | + |
| APRGVPQIEL | 48 | ND | + |
| APRALVETL | 49 | + | + |
| APRMPEAAL | 50 | ND | + |
| APRRLGCEL | 51 | + | + |
| APRPWTPCL | 52 | + | + |
| APRASSPLL | 53 | ND | + |
| APRQLGREL | 54 | ND | + |
| APREISSMVL | 55 | + | + |
| APRSLGLEL | 56 | ++ | + |
| APRTKAEML | 57 | + | + |

- = RA > 10, + = 1 < RA < 10, ++ = RA < 1, Immunogenicity was tested as described in Example 2. +: means that a specific immunoresponse was generated in at least one HLA-B*0702 transgenic mice, ND: Not Determined

Example 4

In Vivo Immunogenicity of Peptides with Enhanced Affinity and Recognition of the Native Counterpart HLA-B7 transgenic mice were vaccinated with the selected peptides, and eleven days later, their spleen cells were in vitro stimulated with the peptide.

Figure 2:
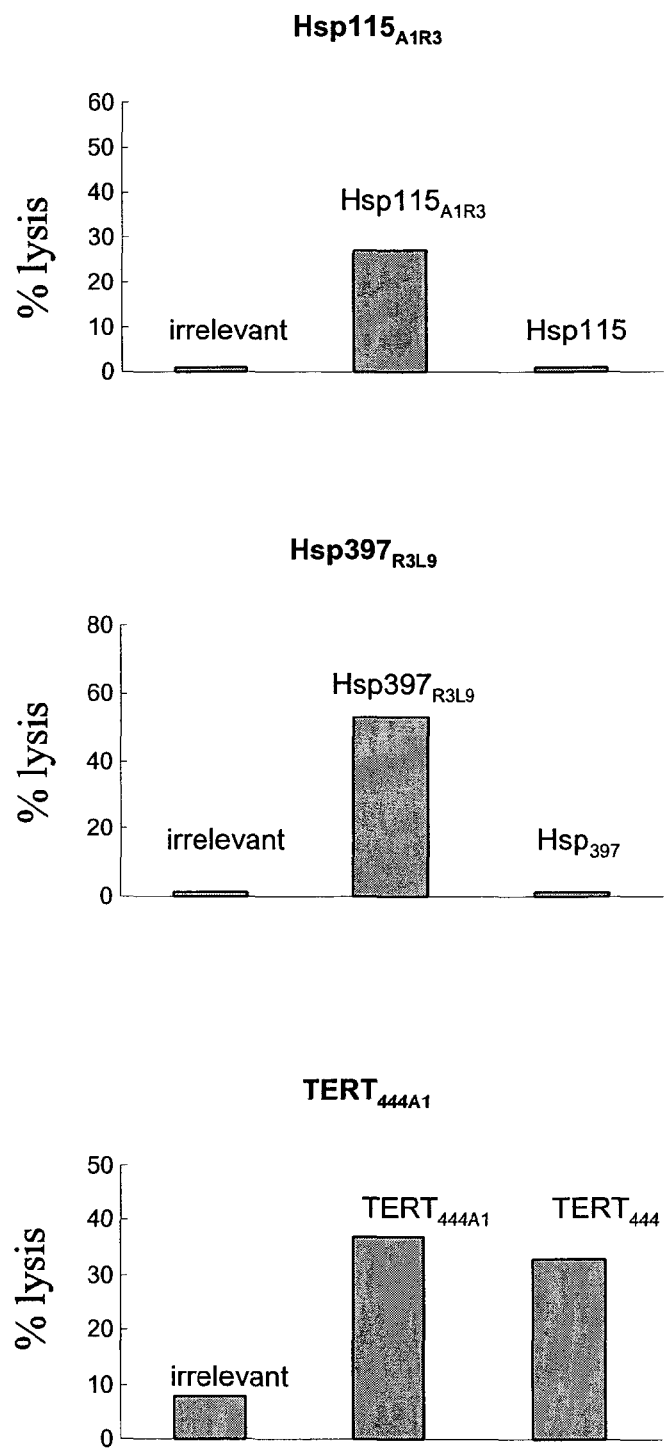
FIG. 2: Immunogenicity of optimized HLA-B*0702 cryptic peptides. CTL were tested against RMA-B7 targets loaded with peptide as indicated.

In this context, $Hsp70_{115}$, $Hsp70_{397}$ and $TERT_{444}$, were therefore modified at position 1 (substitution of the amino acid by an A) and/or position 3 (substitution of the amino acid by an R). For peptide $Hsp70_{397}$ an additional modification at C-terminal position (substitution of the T by an L) has been introduced. Modified peptides i.e. $Hsp70_{115A1R3}$ (SEQ ID NO: 55), $Hsp70_{397R3L9}$ (SEQ ID NO: 56), $TERT_{444A1}$ (SEQ ID NO: 5) exhibited a strong affinity for HLA-B*0702 (Table IV) and induced an immune response in the majority of vaccinated mice (FIG. 2). However, for all peptides but $TERT_{444A1}$, generated CTL recognized the optimized peptide but not the corresponding native peptide (FIG. 2). This strongly suggests that substitution of the amino acid at position 3 by an R may change the conformation of the peptide segment that interacts with the TCR and guarantees TCR cross-recognition.

Since a) all tested peptides with $APX_3X_4X_5X_6X_7X_8X_9X_{10}X_{11}$ have a high affinity and are immunogenic (Table IV and FIG. 1, 2) and b) substitution of the amino acid at position 3 by an R may break the cross-recognition of the native peptide, the inventors selected native peptides having a P and R at positions 2 and 3 respectively, and they substituted the amino acid at position 1 by an A if the last amino acid was favourable (L, A, I, V or M). Given the high importance of position 3 in both affinity and CTL recognition of HLA-B*0702 restricted peptides inventors selected peptides with the sequence $X_1PX_3$ (wherein $X_1$ is any amino acid and $X_3$ is K, R, H or M; these amino acids have been described as being favourable residues at position 3) and a favourable amino acid (A/I/L/V) at C-terminal position. Peptides with this sequence and low affinity for HLA-B*0702 have been modified by substitution of the first residue by an A. This is the case of $TERT_{444}$, $Her-2/neu_{760}$ and $Her-2/neu_{246}$. Inventors also selected peptides with the sequence $APX_3$ (wherein $X_3$ is K, R, H or M) and a non favourable residue at C-terminal position (i.e., an amino acid other than L, A, I, V or M). Peptides with this sequence and low affinity for HLA-B*0702 have been modified by substituting residue at C-terminal position with a L. This is the case of Her-2/neu$_{1069}$. All these modified peptides had a strong affinity for HLA-B*0702.

Example 5

Figure 3:
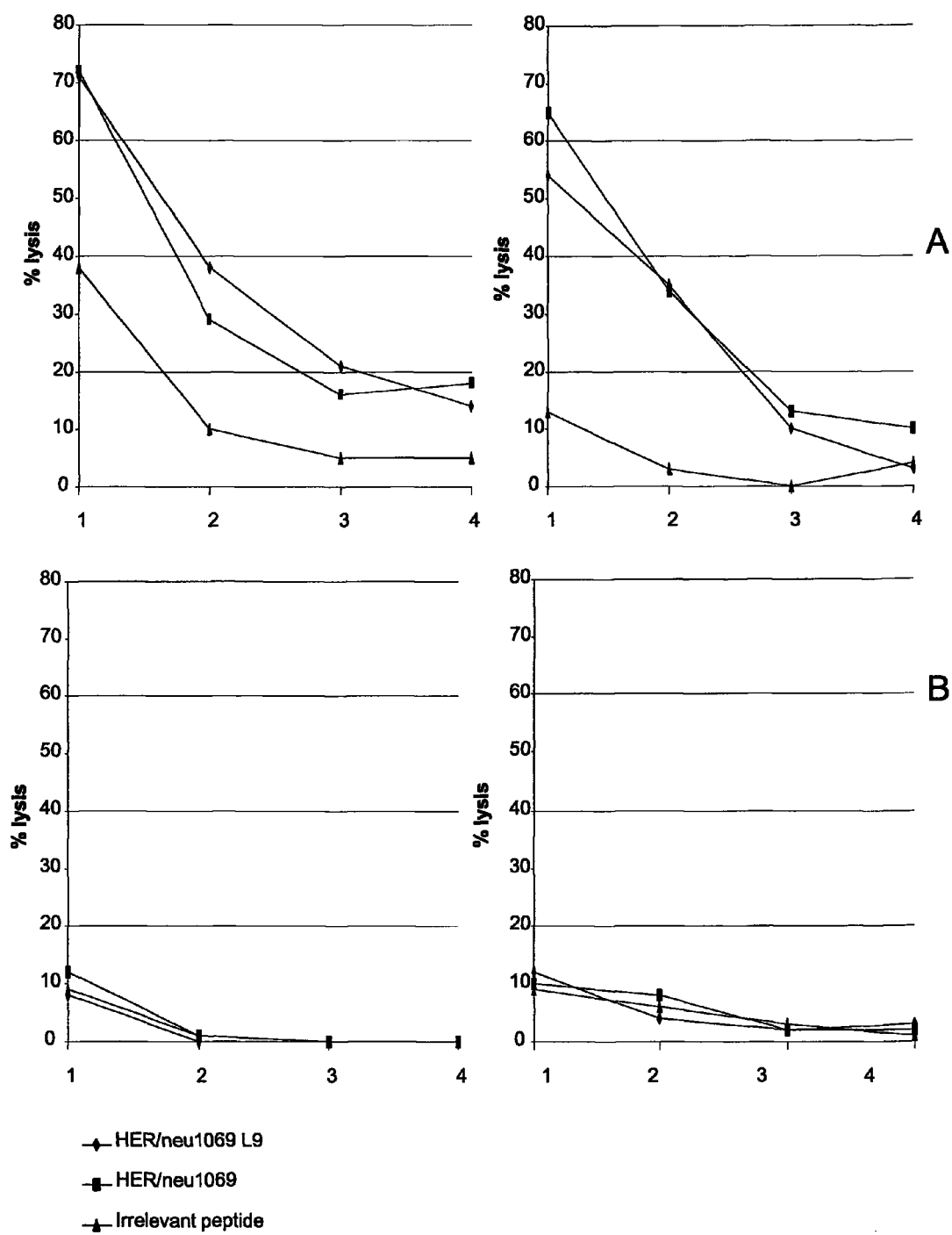
FIG. 3: In vivo immunogenicity of optimized HLA-B*0702Her2neu$_{1069L9}$ (A) and Her2/neu$_{1069}$ (B) peptides in HLA-B*0702 transgenic mice. CTL were tested against RMA-B7 targets loaded with peptide as indicated. CTL population induced was diluted 3 (1), 10 (2), 30 (3) and 100 (4) fold.

Immunogenicity of Optimized Peptides and Cross-Recognition of the Native Counterpart Native Her2/neu$_{246}$, Her2/neu$_{760}$, Her2/neu$_{1069}$ and TERT$_{444}$ peptides were not immunogenic, whereas the optimized peptides were immunogenic in HLA-B*0702 transgenic mice. Moreover, CTL induced by all these optimized peptides were able to cross-react with the corresponding native peptide (FIG. 3 and Table V).

TABLE V

Immunogenicity of native and optimized HLA-B*0702 restricted peptides.

| Peptide | Sequence | SEQ ID NOs: | Immuno-genicity | Corresponding native peptide cross-reconnaissance |
|---|---|---|---|---|
| TERT$_{444}$ | DPRRLVQLL | 1 | − | |
| TERT$_{444A1}$ | APRRLVQLL | 5 | + | + |
| Her2/neu$_{760}$ | SPKANKEIL | 3 | − | |
| Her2/neu$_{760A1}$ | APKANKEIL | 7 | + | + |
| Her2/neu$_{246}$ | GPKHSDCLA | 4 | − | |
| Her2/neu$_{246A1}$ | APKHSDCLA | 8 | + | + |
| Her2/neu$_{1069}$ | APRSPLAPS | 2 | − | |
| Her2/neu$_{1069L9}$ | APRSPLAPL | 6 | + | + |

+ for immunogenicity or native peptide cross recognition means that the peptide induced a specific response in at least one HLA-B*0702 transgenic mouse, able to recognized the corresponding native peptide.

In conclusion, the inventors have described a method to optimize immunogenicity (and also affinity) of HLA-B*0702 restricted cryptic peptides. It consists in a) substituting the residue at position 1 with an A in all peptides comprising the sequence $X_1PX_3$ (wherein $X_1$ is any amino acid except A and $X_3$ is R or K or H or M), a favourable amino acid at C-terminal position (i.e., L or A or I or V or M), and a low affinity for HLA-B*0702, or b) substituting the residue at C-terminal position with a L in peptides comprising the sequence $APX_3$ ($X_3$ being defined as above), a non favourable residue at C-terminal position (i.e., an amino acid other that L or A or I or V or M), and a low affinity for HLA-B*0702.

Example 6

TERT$_4$ Immunodominant Peptide Induces TERT Specific CTL

Figure 4:
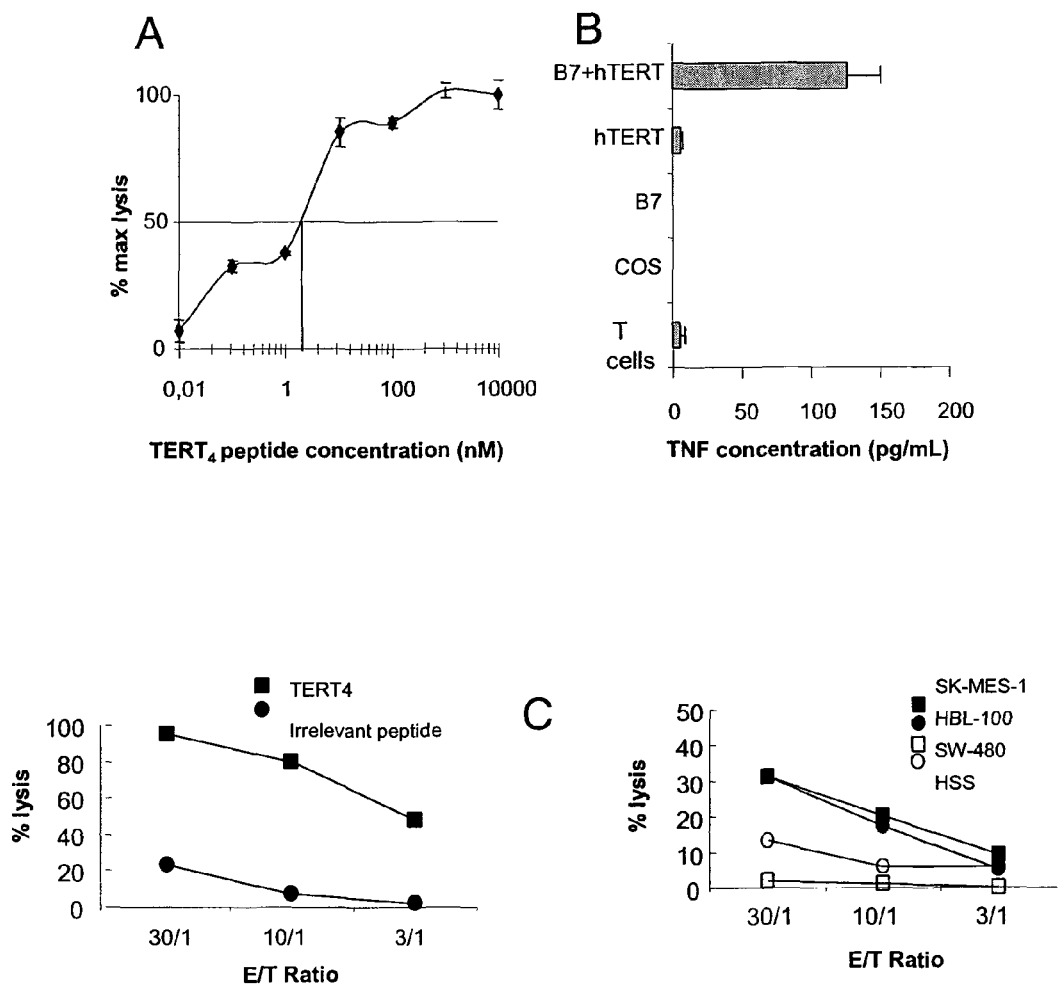
FIG. 4: TERT$_4$ induces TERT specific CTL in HLA-B7 mice and in healthy donors. (A) TERT$_4$ immunogenicity in HLA-B*0702 transgenic mice. CTL were tested against RMA-B7 targets loaded with decreasing doses of TERT$_4$ peptide. (B) Recognition of endogenous TERT by TERT$_4$ specific murine CTL. CTL were tested against COS cells transfected with HLA-B*0702 and TERT as indicated. (C) Induction of TERT$_4$ specific human CTL. CTL were tested against T2-B7 targets loaded with TERT$_4$ (■) or an irrelevant (●) peptide using the Effector/Target ratio as indicated (left graph), and against the HLA-B*0702 positive TERT positive SK-MES-1 (■), HBL-100 (●) and the HLA-B*0702 negative TERT positive SW-480 (□), HSS (○) human tumor cell lines (right graph).

HLA-B7 transgenic mice were then immunized with the TERT$_4$ (SEQ ID NO: 15) and eleven days later their spleen cells were in vitro stimulated with the peptide. Generated CTL killed RMA-B7 targets loaded with decreasing concentrations of TERT$_4$ peptide (FIG. 4A). The half maximal lysis of TERT$_4$ loaded targets was obtained with 1.5 nM (FIG. 4A). CTL were then tested for their capacity to recognize COS-7 cells expressing HLA-B*0702 and endogenous TERT. Results presented in FIG. 4B show that CTL recognized COS-7 cells transfected with both HLA-B*0702 and TERT but not COS-7 cells transfected with either HLA-B*0702 or TERT, demonstrating that TERT$_4$ dominant peptide is an HLA-B*0702 restricted epitope naturally processed from endogenous TERT.

Moreover, CD8 cells from healthy donors were in vitro stimulated with autologous dendritic cells loaded with TERT$_4$ peptide. After four stimulations, CTL were tested for cytotoxicity against TERT$_4$ loaded T2-B7 targets. Three donors were tested and CTL were induced in two of them. Results from one responding donor are presented in FIG. 4C. CTL killed T2-B7 targets presenting TERT$_4$ but not T2-B7 cells presenting the irrelevant Nef peptide (left graph). Interestingly, CTL killed the HLA-B*0702 TERT+ SK-MES-1 and HBL-100 but not the HLA-B*0702-TERT+ SW-480 and HSS human tumor cell lines confirming the HLA-B*0702 restricted presentation and the endogenous processing of the TERT$_4$ epitope (right graph).

Example 7

CTL Induced by TERT$_{444A1}$ Peptide Recognize Endogenous TERT

Figure 5:
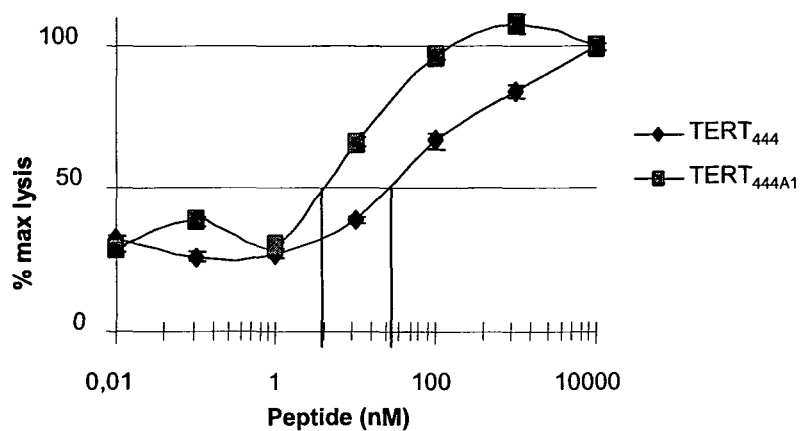
FIG. 5: Recognition of endogenous TERT by TERT$_{444}$ specific murine CTL. (A) CTL were tested against RMA-B7 targets loaded with decreasing doses of TERT$_{444}$ or TERT$_{444A1}$ peptides as indicated. (B) CTL were tested against COS cells transfected with HLA-B*0702 and/or TERT as indicated.
Figure 5:
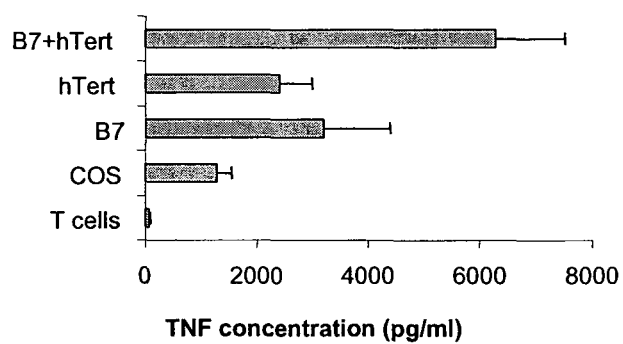

TERT$_{444A1}$ (SEQ ID NO: 5) was tested for its ability to induce CTL able to recognize endogenous TERT and to induce CTL in healthy donors (Example 6). HLA-B*0702 transgenic mice were then immunized with the TERT$_{444A1}$ and eleven days later their spleen cells were in vitro stimulated with the native TERT$_{444}$ peptide (SEQ ID NO: 1). Generated CTL killed RMA-B7 targets loaded with decreasing concentrations of TERT$_{444A1}$ and TERT$_{444}$ peptides. The half maximal lysis of TERT$_{444}$ loaded and TERT$_{444A1}$ loaded targets was obtained with 5.5 nM and 1 nM respectively (FIG. 5A). CTL were then tested for their capacity to recognize COS-7 cells expressing HLA-B*0702 and endogenous TERT. Results presented in FIG. 5B show that CTL recognized COS-7 cells transfected with both HLA-B*0702 and TERT but not COS-7 cells transfected with either HLA-B*0702 or TERT demonstrating that TERT$_{444}$ is an HLA-B*0702 restricted cryptic epitope naturally processed from endogenous TERT.

Example 8

TERT$_{444A1}$ Stimulates CTL from Health Donors

Figure 6:
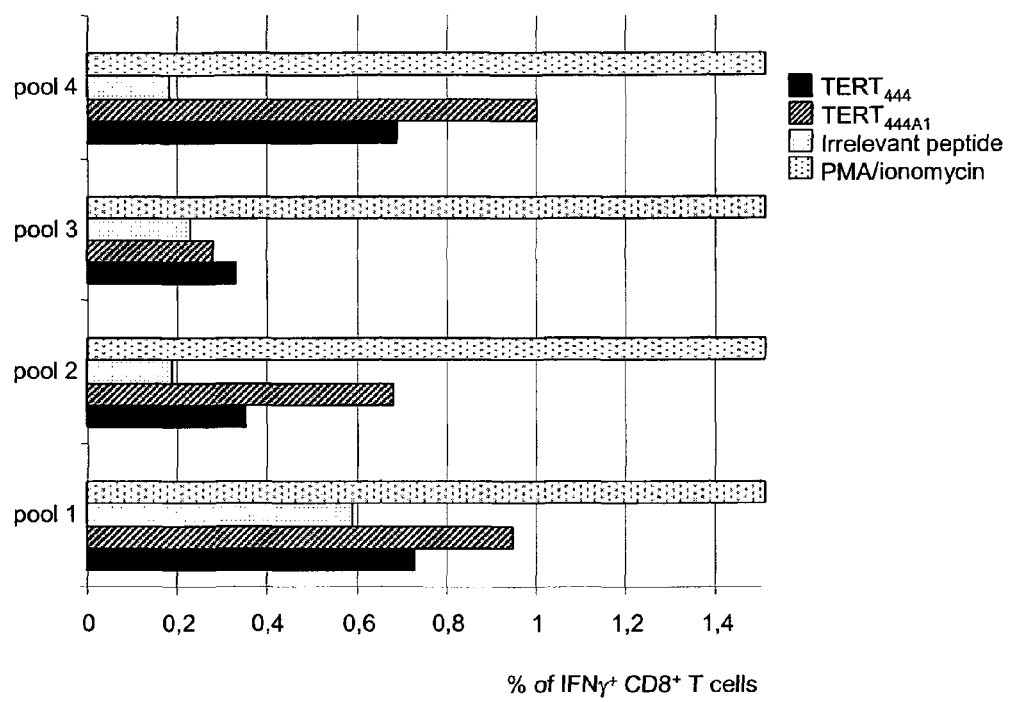
FIG. 6: Induction of TERT$_{444A1}$ specific human CTL. CTL were tested against T2-B7 targets loaded with peptides as indicated. CTL maximal activation is obtained by PMA/ionomycin treatment.

CD8 cells from healthy donors were in vitro stimulated with autologous dendritic cells loaded with TERT$_{444A1}$ peptide. After four stimulations, proliferating cells were divided into 4 pools. Each pool was then tested for intracellular IFNg production upon stimulation with T2-B7 cells loaded with optimized TERT$_{444A1}$ or native TERT$_{444}$. Results from D5609 responding donor are presented in FIG. 6. IFNg producing CTL were detected in pools 2 and 4 after stimulation with either TERT$_{444}$ or TERT$_{444A1}$ loaded T2B7 cells (FIG. 6).

REFERENCES

Anderton, S. M., Viner, N. J., Matharu, P., Lowrey, P. A., and Wraith, D.C. (2002). Influence of a dominant cryptic epitope on autoimmune T cell tolerance. Nat Immunol 3, 175-181.

Bakker, A. B., van der Burg, S. H., Huijbens, R. J., Drijfhout, J. W., Melief, C. J., Adema, G. J., and Figdor, C. G.

(1997). Analogues of CTL epitopes with improved MHC class-I binding capacity elicit anti-melanoma CTL recognizing the wild-type epitope. Int J Cancer 70, 302-309.

Boisgérault, F., Anosova, N. G., Tam, R. C., Illigens, B. M., Fedoseyeva, E. V., and Benichou, G. (2000). Induction of T-cell response to cryptic MHC determinants during allograft rejection. Hum Immunol 61, 1352-1362.

Bowne, W. B., Srinivasan, R., Wolchok, J. D., Hawkins, W. G., Blachere, N. E., Dyall, R., Lewis, J. J., and Houghton, A. N. (1999). Coupling and uncoupling of tumor immunity and autoimmunity. J Exp Med 190, 1717-1722.

Cibotti, R., Kanellopoulos, J. M., Cabaniols, J. P., Halle-Panenko, O., Kosmatopoulos, K., Sercarz, E., and Kourilsky, P. (1992). Tolerance to a self-protein involves its immunodominant but does not involve its subdominant determinants. Proc Natl Acad Sci USA 89, 416-420.

Colella, T. A., Bullock, T. N., Russell, L. B., Mullins, D. W., Overwijk, W. W., Luckey, C. J., Pierce, R. A., Restifo, N. P., and Engelhard, V. H. (2000). Self-tolerance to the murine homologue of a tyrosinase-derived melanoma antigen: implications for tumor immunotherapy. J Exp Med 191, 1221-1232.

Cortez-Gonzalez, X., Sidney, J., Adotevi O., Sette, A., Millard, F., Lemonnier, F., Langlade-Demoyen, P., Zanetti, M. (2006). Immunogenic HLA-B7-restricted peptides of hTRT. Int Immunol 18, 1707-1718.

Disis, M. L., Gooley, T. A., Rinn, K., Davis, D., Piepkorn, M., Cheever, M. A., Knutson, K. L., and Schiffman, K. (2002). Generation of T-cell immunity to the HER-2/neu protein after active immunization with HER-2/neu peptide-based vaccines. J Clin Oncol 20, 2624-2632.

Dyall, R., Bowne, W. B., Weber, L. W., LeMaoult, J., Szabo, P., Moroi, Y., Piskun, G., Lewis, J. J., Houghton, A. N., and Nikolic-Zugic, J. (1998). Heteroclitic immunization induces tumor immunity. J Exp Med 188, 1553-1561.

Engelhom, M. E., Guevara-Patino, J. A., Noffz, G., Hooper, A. T., Lou, O., Gold, J. S., Kappel, B. J., and Houghton, A. N. (2006). Autoimmunity and tumor immunity induced by immune responses to mutations in self. Nat Med 12, 198-206.

Espevik, T., and Nissen-Meyer, J. (1986). A highly sensitive cell line, WEHI 164 clone 13, for measuring cytotoxic factor/tumor necrosis factor from human monocytes J Immunol Methods 95, 99-105.

Friedman, R. S., Spies, A. G., and Kalos, M. (2004). Identification of naturally processed CD8 T cell epitopes from prostein, a prostate tissue-specific vaccine candidate. Eur J Immunol 34, 1091-1101.

Gaugler, B., Brouwenstijn, N., Vantomme, V., Szikora, J. P., Van der Spek, C. W., Patard, J. J., Boon, T., Schrier, P., Van den Eynde, B. J. A new gene coding for an antigen recognized by autologous cytolytic T lymphocytes on a human renal carcinoma. (1996) Immunogenetics 44, 323-30

Gross, D. A., Graff-Dubois, S., Opolon, P., Comet, S., Alves, P., Bennaceur-Griscelli, A., Faure, O., Guillaume, P., Firat, H., Chouaib, S., et al. (2004). High vaccination efficiency of low-affinity epitopes in antitumor immunotherapy. J Clin Invest 113, 425-433.

Grossmann, M. E., Davila, E., and Celis, E. (2001). Avoiding Tolerance Against Prostatic Antigens With Subdominant Peptide Epitopes. J Immunother 24, 237-241.

Hawkins, W. G., Gold, J. S., Dyall, R., Wolchok, J. D., Hoos, A., Bowne, W. B., Srinivasan, R., Houghton, A. N., and Lewis, J. J. (2000). Immunization with DNA coding for gp100 results in CD4 T-cell independent antitumor immunity. Surgery 128, 273-280.

Hernandez, J., Lee, P. P., Davis, M. M., and Sherman, L. A. (2000). The use of HLA A2.1/p53 peptide tetramers to visualize the impact of self tolerance on the TCR repertoire. J Immunol 164, 596-602.

Lally, K. M., Mocellin, S., Ohnmacht, G. A., Nielsen, M. B., Bettinotti, M., Panelli, M. C., Monsurro, V., and Marincola, F. M. (2001). Unmasking cryptic epitopes after loss of immunodominant tumor antigen expression through epitope spreading. Int J Cancer 93, 841-847.

Lennerz V., Fatho M., Gentilini C., Frye R. A., Lifke A., Ferel D., Wölfel C., Huber C., Wölfel T. (2005). The response of autologous T cells to a human melanoma is dominated by mutated neoantigens. PNAS U.S.A. 102, 16013-8

Lu, J., Celis, E. (2000). Use of two predictive algorithms of the world wide web for the identification of tumor-reactive T-cell epitopes. Cancer Res. 60, 5223-5227.

Luiten, R., van der Bruggen, P. (2000). A MAGE-A1 peptide is recognized on HLA-B7 human tumors by cytolytic T lymphocytes. Tissue antigens 55, 149-152.

Meyerson, M., Counter, C. M., Eaton, E. N., Ellisen, L. W., Steiner, P., Caddie, S. D., Ziaugra, L., Beijersbergen, R. L., Davidoff, M. J., Liu, Q., et al. (1997). hEST2, the putative human telomerase catalytic subunit gene, is up-regulated in tumor cells and during immortalization. Cell 90, 785-795.

Moudgil, K. D., and Sercarz, E. E. (1994a). Can antitumor immune responses discriminate between self and nonself? Immunol Today 15, 353-355.

Moudgil, K. D., and Sercarz, E. E. (1994b). The T cell repertoire against cryptic self determinants and its involvement in autoimmunity and cancer. Clin Immunol Immunopathol 73, 283-289.

Moudgil, K. D., Southwood, S., Ametani, A., Kim, K., Sette, A., and Sercarz, E. E. (1999). The self-directed T cell repertoire against mouse lysozyme reflects the influence of the hierarchy of its own determinants and can be engaged by a foreign lysozyme. J Immunol 163, 4232-4237.

Naftzger, C., Takechi, Y., Kohda, H., Hara, I., Vijayasaradhi, S., and Houghton, A. N. (1996). Immune response to a differentiation antigen induced by altered antigen: a study of tumor rejection and autoimmunity. Proc Natl Acad Sci U S A 93, 14809-14814.

Overwijk, W. W., Theoret, M. R., Finkelstein, S. E., Surman, D. R., de Jong, L. A., Vyth-Dreese, F. A., Dellemijn, T. A., Antony, P. A., Spiess, P. J., Palmer, D.C., et al. (2003). Tumor regression and autoimmunity after reversal of a functionally tolerant state of self-reactive CD8+ T cells. J Exp Med 198, 569-580.

Overwijk, W. W., Tsung, A., Irvine, K. R., Parkhurst, M. R., Goletz, T. J., Tsung, K., Carroll, M. W., Liu, C., Moss, B., Rosenberg, S. A., and Restifo, N. P. (1998). gp100/pmel 17 is a murine tumor rejection antigen: induction of "self"-reactive, tumoricidal T cells using high-affinity, altered peptide ligand. J Exp Med 188, 277-286.

Palomba, M. L., Roberts, W. K., Dao, T., Manukian, G., Guevara-Patino, J. A., Wolchok, J. D., Scheinberg, D. A., and Houghton, A. N. (2005). CD8+ T-cell-dependent immunity following xenogeneic DNA immunization against CD20 in a tumor challenge model of B-cell lymphoma. Clin Cancer Res 11, 370-379.

Parker, K. C., Bednarek, M. A., Coligan J. E. (1994). Scheme for ranking potential HLA-A2 binding peptides based on independent binding of individual peptide sidechains. J Immunol 152, 163-175.

Parkhurst, M. R., Salgaller, M. L., Southwood, S., Robbins, P. F., Sette, A., Rosenberg, S. A., and Kawakami, Y. (1996). Improved induction of melanoma-reactive CTL with peptides from the melanoma antigen gp100 modified at HLA-A*0201-binding residues. J Immunol 157, 2539-2548.

Paterson, Y., and Maciag, P. C. (2005). Listeria-based vaccines for cancer treatment. Curr Opin Mol Ther 7, 454-460.

Rammensee, H., Bachmann, J., Emmerich, N. P., Bachor, O. A., Stevanovic, S. (1999). SYFPEITHI: database for MHC ligands and peptide motifs. Immunogenetics. 50, 213-219.

Rohrlich, P. S., Cardinaud, S., Firat, H., Lamari, M., Briand, P., Escriou, N., and Lemonnier, F. A. (2003). HLA-B*0702 transgenic, H-2 KbDb double-knockout mice: phenotypical and functional characterization in response to influenza virus. Int Immunol 15, 765-772.

Ronsin, C., Chung-Scott, V., Poullion, I., Aknouche, N., Gaudin, C., Triebel, F. (1999). A non-AUG-defined alternative open reading frame of the intestinal carboxyl esterase mRNA generates an epitope recognized by renal cell carcinoma-reactive tumor-infiltrating lymphocytes in situ. J Immunol 163, 483-90

Sarobe, P., Pendleton, C. D., Akatsuka, T., Lau, D., Engelhard, V. H., Feinstone, S. M., and Berzofsky, J. A. (1998). Enhanced in vitro potency and in vivo immunogenicity of a CTL epitope from hepatitis C virus core protein following amino acid replacement at secondary HLA-A2.1 binding positions. J Clin Invest 102, 1239-1248.

Scardino, A., Gross, D. A., Alves, P., Schultze, J. L., Graff-Dubois, S., Faure, O., Tourdot, S., Chouaib, S., Nadler, L. M., Lemonnier, F. A., et al. (2002). HER-2/neu and hTERT cryptic epitopes as novel targets for broad spectrum tumor immunotherapy. J Immunol 168, 5900-5906.

Sidney, J., Southwood, S., del Guercio, M. F., Grey, H. M., Chesnut, R. W., Kubo, R. T., and Sette, A. (1996). Specificity and degeneracy in peptide binding to HLA-B7-like class I molecules. J Immunol 157, 3480-3490.

Sinha, P., Chi, H. H., Kim, H. R., Clausen, B. E., Pederson, B., Sercarz, E. E., Forster, I., and Moudgil, K. D. (2004). Mouse lysozyme-M knockout mice reveal how the self-determinant hierarchy shapes the T cell repertoire against this circulating self antigen in wild-type mice. J Immunol 173, 1763-1771.

Slager, E. H., van der Minne, C. E., Goudsmit, J., van Oers J., M., Kostense, S., Havenga, M. J., Osanta, S., and Griffioen, M. (2004). Induction of CAMEL/NY-ESO-ORF2-specific CD8+ T cells upon stimulation with dendritic cells infected with a modified Ad5 vector expressing a chimeric Ad5/35 fiber. Cancer Gene Ther 11, 227-236.

Theobald, M., Biggs, J., Hernandez, J., Lustgarten, J., Labadie, C., and Sherman, L. A. (1997). Tolerance to p53 by A2.1-restricted cytotoxic T lymphocytes. J Exp Med 185, 833-841.

Tourdot, S., Scardino, A., Saloustrou, E., Gross, D. A., Pascolo, S., Cordopatis, P., Lemonnier, F. A., and Kosmatopoulos, K. (2000). A general strategy to enhance immunogenicity of low-affinity HLA-A2. 1-associated peptides: implication in the identification of cryptic tumor epitopes. Eur J Immunol 30, 3411-3421.

Valmori, D., Fonteneau, J. F., Lizana, C. M., Gervois, N., Lienard, D., Rimoldi, D., Jongeneel, V., Jotereau, F., Cerottini, J. C., and Romero, P. (1998). Enhanced generation of specific tumor-reactive CTL in vitro by selected Melan-A/MART-1 immunodominant peptide analogues. J Immunol 160, 1750-1758.

Van Den Eynde, B. J., Gaugler, B., Probst-Kepper, M., Michaux, L., Devuyst, O., Lorge., F, Weynants., P, Boon, T. (1999). A new antigen recognized by cytolytic T lymphocytes on a human kidney tumor results from reverse strand transcription. J. Exp. Med 190, 1793-1800.

Vierboom, M. P., Nijman, H. W., Offiing a, R., van der Voort, E. I., van Hall, T., van den Broek, L., Fleuren, G. J., Kenemans, P., Kast, W. M., and Melief, C. J. (1997). Tumor eradication by wild-type p53-specific cytotoxic T lymphocytes. J Exp Med 186, 695-704.

Weber, L. W., Bowne, W. B., Wolchok, J. D., Srinivasan, R., Qin, J., Moroi, Y., Clynes, R., Song, P., Lewis, J. J., and Houghton, A. N. (1998). Tumor immunity and autoimmunity induced by immunization with homologous DNA. J Clin Invest 102, 1258-1264.

Worley, B. S., van den Broeke, L. T., Goletz, T. J., Pendleton C. D., Daschbach, E. M., Thomas E. K., Marincola, F. M., Helman L. J., and Berzofsky, J. A. (2001). Antigenicity of fusion proteins from sarcoma-associated chromosomal translocations. Cancer Res 61, 6868-6875.

The invention claimed is:

1. A cryptic HLA-B*0702-restricted epitope consisting of APRSPLAPS (SEQ ID NO: 2).

2. An immunogenic HLA-B*0702-restricted epitope, which is derived from the cryptic HLA-B*0702-restricted epitope APRSPLAPS (SEQ ID NO: 2), by substituting its C-terminal amino-acid with a leucine.

3. A chimeric polypeptide, comprising the cryptic HLB-B*0702-restricted epitope according to claim 1 and one, two, or more HLA-B*0702-restricted cryptic epitopes selected from the group consisting of APRSPLAPS (SEQ ID NO: 2), SPKANKEIL (SEQ ID NO: 3), GPKHSDCLA (SEQ ID NO: 4), and DPRRLVQLL (SEQ ID NO: 1).

4. A chimeric polypeptide, comprising the immunogenic HLA-B*0702-restricted epitope according to claim 2 and one, two, or more immunogenic HLA-B*0702-restricted epitopes selected from the group consisting of APRSPLAPL (SEQ ID NO: 6), APKANKEIL (SEQ ID NO: 7), APKHSD-CLA (SEQ ID NO: 8), and APRRLVQLL (SEQ ID NO: 5).

5. A pharmaceutical composition comprising at least, as an active principle, a HLA-B*0702-restricted cryptic epitope according to claim 1.

6. The pharmaceutical composition of claim 5, which is a vaccine.

7. A kit of parts comprising, in separate formulations, a first peptide having the sequence APRSPLAPS (SEQ ID NO: 2), and a second peptide having the sequence APRSPLAPL (SEQ ID NO: 6).

8. A kit of parts comprising, in separate formulations, a first chimeric polypeptide according to claim 3, and a second chimeric polypeptide comprising the immunogenic HLA-B*0702-restricted epitope APRSPLAPL (SEQ ID NO: 6) and one, two, or more immunogenic HLA-B*0702-restricted epitopes selected from the group consisting of APRSPLAPL (SEQ ID NO: 6), APKANKEIL (SEQ ID NO: 7), APKHSD-CLA (SEQ ID NO: 8), and APRRLVQLL (SEQ ID NO: 5), wherein the HLA-B*0702-restricted immunogenic epitopes of the second chimeric polypeptide are cognate to the HLA-B*0702-restricted cryptic epitopes comprised in the first chimeric polypeptide.

9. The kit according to claim 7, which is a vaccination kit, wherein said first and second peptides or chimeric polypeptides are in separate vaccination doses.

10. The vaccination kit according to claim 9, which comprises 2 or 3 doses of second peptide or chimeric polypeptide, and 3, 4, 5, 6 or up to 50 doses of first peptide.

11. The vaccination kit according to claim 9, wherein each dose comprises 1 to 5 mg of peptide.

12. The vaccination kit according to claim 9, wherein the vaccination doses are formulated for subcutaneous injection.

13. A pharmaceutical composition comprising at least, as an active principle, an immunogenic epitope according to claim 2.

14. A pharmaceutical composition comprising at least, as an active principle, a chimeric polypeptide according to claim 3.

15. A pharmaceutical composition comprising at least, as an active principle, a chimeric polypeptide according to claim 4.

16. The kit according to claim 8, which is a vaccination kit, wherein said first and second chimeric polypeptides are in separate vaccination doses.

17. The vaccination kit according to claim 16, which comprises 2 or 3 doses of second chimeric polypeptide, and 3, 4, 5, 6 or up to 50 doses of first chimeric polypeptide.

18. The vaccination kit according to claim 16, wherein each dose comprises 1 to 20 mg of chimeric polypeptide.

19. The vaccination kit according to claim 16, wherein the vaccination doses are formulated for subcutaneous injection.

\* \* \* \* \*

UNITED STATES PATENT AND TRADEMARK OFFICE
CERTIFICATE OF CORRECTION

PATENT NO. : 8,465,747 B2
APPLICATION NO. : 12/373408
DATED : June 18, 2013
INVENTOR(S) : Kostantinos Kostas Kosmatopoulos et al.

It is certified that error appears in the above-identified patent and that said Letters Patent is hereby corrected as shown below:

In the Claims:

In Claim 9, at Column 41, line 26, delete "peptides or chimeric polypeptides are"

and replace it with --peptides are--.

In Claim 10, at Column 42, line 2, delete "peptide or chimeric polypeptide, and"

and replace it with --peptide, and--.

Signed and Sealed this
Third Day of September, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,465,747 B2  
APPLICATION NO. : 12/373408  
DATED : June 18, 2013  
INVENTOR(S) : Kosmatopoulos et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this

Eighth Day of September, 2015

Michelle K. Lee  
*Director of the United States Patent and Trademark Office*

SEQUENCE LISTING

```
<160> NUMBER OF SEQ ID NOS: 61

<210> SEQ ID NO 1
<211> LENGTH: 9
<212> TYPE: PRT
<213> ORGANISM: Artificial
<220> FEATURE:
<223> OTHER INFORMATION: cryptic peptide TERT444

<400> SEQUENCE: 1

Asp Pro Arg Arg Leu Val Gln Leu Leu
1               5

<210> SEQ ID NO 2
<211> LENGTH: 9
<212> TYPE: PRT
<213> ORGANISM: Artificial
<220> FEATURE:
<223> OTHER INFORMATION: HER-2/neu1069 HLA-B*0702 restricted cryptic
      epitope

<400> SEQUENCE: 2
```

```
Ala Pro Arg Ser Pro Leu Ala Pro Ser
1               5

<210> SEQ ID NO 3
<211> LENGTH: 9
<212> TYPE: PRT
<213> ORGANISM: Artificial
<220> FEATURE:
<223> OTHER INFORMATION: HER-2/neu760 HLA-B*0702 restricted cryptic
      epitope

<400> SEQUENCE: 3

Ser Pro Lys Ala Asn Lys Glu Ile Leu
1               5

<210> SEQ ID NO 4
<211> LENGTH: 9
<212> TYPE: PRT
<213> ORGANISM: Artificial
<220> FEATURE:
<223> OTHER INFORMATION: HER-2/neu246 HLA-B*0702 restricted cryptic
      epitope

<400> SEQUENCE: 4

Gly Pro Lys His Ser Asp Cys Leu Ala
1               5

<210> SEQ ID NO 5
<211> LENGTH: 9
<212> TYPE: PRT
<213> ORGANISM: Artificial
<220> FEATURE:
<223> OTHER INFORMATION: TERT444A1/optimized peptide derived from the
      cryptic peptide of SEQ ID NO:1

<400> SEQUENCE: 5

Ala Pro Arg Arg Leu Val Gln Leu Leu
1               5

<210> SEQ ID NO 6
<211> LENGTH: 9
<212> TYPE: PRT
<213> ORGANISM: Artificial
<220> FEATURE:
<223> OTHER INFORMATION: Her-2/neu1069L9 optimized peptide derived from
      the cryptic peptide of SEQ ID NO:2

<400> SEQUENCE: 6

Ala Pro Arg Ser Pro Leu Ala Pro Leu
1               5

<210> SEQ ID NO 7
<211> LENGTH: 9
<212> TYPE: PRT
<213> ORGANISM: Artificial
<220> FEATURE:
<223> OTHER INFORMATION: Her-2/neu760A1 optimized peptide derived from
      the cryptic peptide of SEQ ID NO:3

<400> SEQUENCE: 7

Ala Pro Lys Ala Asn Lys Glu Ile Leu
1               5

<210> SEQ ID NO 8
<211> LENGTH: 9
<212> TYPE: PRT
<213> ORGANISM: Artificial
<220> FEATURE:
<223> OTHER INFORMATION: Her-2/neu246A1 optimized peptide derived from
```

-continued the cryptic peptide of SEQ ID NO:4

<400> SEQUENCE: 8

Ala Pro Lys His Ser Asp Cys Leu Ala
1               5

<210> SEQ ID NO 9
<211> LENGTH: 10
<212> TYPE: PRT
<213> ORGANISM: Artificial
<220> FEATURE:
<223> OTHER INFORMATION: reference peptide CMV265-274 (R10V)

<400> SEQUENCE: 9

Arg Pro His Glu Arg Asn Gly Phe Thr Val
1               5                   10

<210> SEQ ID NO 10
<211> LENGTH: 13
<212> TYPE: PRT
<213> ORGANISM: Artificial
<220> FEATURE:
<223> OTHER INFORMATION: I-AB restricted HBVcore128 T helper epitope

<400> SEQUENCE: 10

Thr Pro Pro Ala Tyr Arg Pro Pro Asn Ala Pro Ile Leu
1               5                   10

<210> SEQ ID NO 11
<211> LENGTH: 10
<212> TYPE: PRT
<213> ORGANISM: Artificial
<220> FEATURE:
<223> OTHER INFORMATION: peptide of Hsp70_115

<400> SEQUENCE: 11

Tyr Pro Glu Glu Ile Ser Ser Met Val Leu
1               5                   10

<210> SEQ ID NO 12
<211> LENGTH: 10
<212> TYPE: PRT
<213> ORGANISM: Artificial
<220> FEATURE:
<223> OTHER INFORMATION: HSP70_115A1 optimized peptide

<400> SEQUENCE: 12

Ala Pro Glu Glu Ile Ser Ser Met Val Leu
1               5                   10

<210> SEQ ID NO 13
<211> LENGTH: 10
<212> TYPE: PRT
<213> ORGANISM: Artificial
<220> FEATURE:
<223> OTHER INFORMATION: Hsp70 137(10) antigen peptide

<400> SEQUENCE: 13

Tyr Pro Val Thr Asn Ala Val Ile Thr Val
1               5                   10

<210> SEQ ID NO 14
<211> LENGTH: 9
<212> TYPE: PRT
<213> ORGANISM: Artificial
<220> FEATURE:
<223> OTHER INFORMATION: Hsp70 397 antigen peptide

```
<400> SEQUENCE: 14

Ala Pro Leu Ser Leu Gly Leu Glu Thr
1               5

<210> SEQ ID NO 15
<211> LENGTH: 10
<212> TYPE: PRT
<213> ORGANISM: Artificial
<220> FEATURE:
<223> OTHER INFORMATION: TERT4 antigen peptide

<400> SEQUENCE: 15

Ala Pro Arg Cys Arg Ala Val Arg Ser Leu
1               5                   10

<210> SEQ ID NO 16
<211> LENGTH: 9
<212> TYPE: PRT
<213> ORGANISM: Artificial
<220> FEATURE:
<223> OTHER INFORMATION: MAGE-A121.1 antigen peptide

<400> SEQUENCE: 16

Glu Pro Val Thr Lys Ala Glu Met Leu
1               5

<210> SEQ ID NO 17
<211> LENGTH: 9
<212> TYPE: PRT
<213> ORGANISM: Artificial
<220> FEATURE:
<223> OTHER INFORMATION: MAGE-121.1 A1 optimized peptide

<400> SEQUENCE: 17

Ala Pro Val Thr Lys Ala Glu Met Leu
1               5

<210> SEQ ID NO 18
<211> LENGTH: 9
<212> TYPE: PRT
<213> ORGANISM: Artificial
<220> FEATURE:
<223> OTHER INFORMATION: MAGE-A121.2 antigen peptide

<400> SEQUENCE: 18

Glu Pro Phe Thr Lys Ala Glu Met Leu
1               5

<210> SEQ ID NO 19
<211> LENGTH: 9
<212> TYPE: PRT
<213> ORGANISM: Artificial
<220> FEATURE:
<223> OTHER INFORMATION: MAGE-A121.4 antigen peptide

<400> SEQUENCE: 19

Glu Pro Ile Thr Lys Ala Glu Ile Leu
1               5

<210> SEQ ID NO 20
<211> LENGTH: 9
<212> TYPE: PRT
<213> ORGANISM: Artificial
<220> FEATURE:
<223> OTHER INFORMATION: NY-ESO-1 tumor derived HLA-B*0702 restricted
      epitope

<400> SEQUENCE: 20
```

```
Ala Pro Arg Gly Val Arg Met Ala Asn
1               5

<210> SEQ ID NO 21
<211> LENGTH: 9
<212> TYPE: PRT
<213> ORGANISM: Artificial
<220> FEATURE:
<223> OTHER INFORMATION: ICE tumor derived HLA-B*0702 restricted epitope

<400> SEQUENCE: 21

Ser Pro Arg Trp Trp Pro Thr Cys Leu
1               5

<210> SEQ ID NO 22
<211> LENGTH: 10
<212> TYPE: PRT
<213> ORGANISM: Artificial
<220> FEATURE:
<223> OTHER INFORMATION: RAGE-1 tumor derived HLA-B*0702 restricted
      epitope

<400> SEQUENCE: 22

Ser Pro Ser Ser Asn Arg Ile Arg Asn Thr
1               5                   10

<210> SEQ ID NO 23
<211> LENGTH: 9
<212> TYPE: PRT
<213> ORGANISM: Artificial
<220> FEATURE:
<223> OTHER INFORMATION: RU2AS tumor derived HLA-B*0702 restricted
      epitope

<400> SEQUENCE: 23

Leu Pro Arg Trp Pro Pro Pro Gln Leu
1               5

<210> SEQ ID NO 24
<211> LENGTH: 9
<212> TYPE: PRT
<213> ORGANISM: Artificial
<220> FEATURE:
<223> OTHER INFORMATION: RBAF500 tumor derived HLA-B*0702 restricted
      epitope

<400> SEQUENCE: 24

Arg Pro His Val Pro Glu Ser Ala Phe
1               5

<210> SEQ ID NO 25
<211> LENGTH: 10
<212> TYPE: PRT
<213> ORGANISM: Artificial
<220> FEATURE:
<223> OTHER INFORMATION: SSX2 fusion protein HLA-B*0702 restricted
      epitope

<400> SEQUENCE: 25

Gln Pro Arg Tyr Gly Tyr Asp Gln Ile Met
1               5                   10

<210> SEQ ID NO 26
<211> LENGTH: 10
<212> TYPE: PRT
<213> ORGANISM: Artificial
<220> FEATURE:
<223> OTHER INFORMATION: HIVp17
```

```
<400> SEQUENCE: 26

Arg Pro Gly Gly Lys Lys Arg Tyr Lys Leu
1               5                   10

<210> SEQ ID NO 27
<211> LENGTH: 9
<212> TYPE: PRT
<213> ORGANISM: Artificial
<220> FEATURE:
<223> OTHER INFORMATION: HIVp24

<400> SEQUENCE: 27

Ser Pro Arg Thr Leu Asn Ala Trp Val
1               5

<210> SEQ ID NO 28
<211> LENGTH: 9
<212> TYPE: PRT
<213> ORGANISM: Artificial
<220> FEATURE:
<223> OTHER INFORMATION: HIVp24

<400> SEQUENCE: 28

His Pro Val His Ala Gly Pro Ile Ala
1               5

<210> SEQ ID NO 29
<211> LENGTH: 9
<212> TYPE: PRT
<213> ORGANISM: Artificial
<220> FEATURE:
<223> OTHER INFORMATION: HIVp24

<400> SEQUENCE: 29

Pro Pro Ile Pro Val Gly Glu Ile Tyr
1               5

<210> SEQ ID NO 30
<211> LENGTH: 9
<212> TYPE: PRT
<213> ORGANISM: Artificial
<220> FEATURE:
<223> OTHER INFORMATION: HIVp24

<400> SEQUENCE: 30

Gly Pro Gly His Lys Ala Arg Val Leu
1               5

<210> SEQ ID NO 31
<211> LENGTH: 10
<212> TYPE: PRT
<213> ORGANISM: Artificial
<220> FEATURE:
<223> OTHER INFORMATION: HIV-RT

<400> SEQUENCE: 31

Ser Pro Ile Glu Thr Val Pro Val Lys Leu
1               5                   10

<210> SEQ ID NO 32
<211> LENGTH: 10
<212> TYPE: PRT
<213> ORGANISM: Artificial
<220> FEATURE:
<223> OTHER INFORMATION: HIV-RT

<400> SEQUENCE: 32
```

```
Gly Pro Lys Val Lys Gln Trp Pro Leu Thr
1               5                   10

<210> SEQ ID NO 33
<211> LENGTH: 9
<212> TYPE: PRT
<213> ORGANISM: Artificial
<220> FEATURE:
<223> OTHER INFORMATION: HIV-RT

<400> SEQUENCE: 33

Ser Pro Ala Ile Phe Gln Ser Ser Met
1               5

<210> SEQ ID NO 34
<211> LENGTH: 9
<212> TYPE: PRT
<213> ORGANISM: Artificial
<220> FEATURE:
<223> OTHER INFORMATION: HIV-RT

<400> SEQUENCE: 34

Ile Pro Leu Thr Glu Glu Ala Glu Leu
1               5

<210> SEQ ID NO 35
<211> LENGTH: 10
<212> TYPE: PRT
<213> ORGANISM: Artificial
<220> FEATURE:
<223> OTHER INFORMATION: HIV-RT

<400> SEQUENCE: 35

Gln Pro Asp Lys Ser Glu Ser Glu Leu Val
1               5                   10

<210> SEQ ID NO 36
<211> LENGTH: 10
<212> TYPE: PRT
<213> ORGANISM: Artificial
<220> FEATURE:
<223> OTHER INFORMATION: HIV-Vif

<400> SEQUENCE: 36

His Pro Arg Ile Ser Ser Glu Val His Ile
1               5                   10

<210> SEQ ID NO 37
<211> LENGTH: 10
<212> TYPE: PRT
<213> ORGANISM: Artificial
<220> FEATURE:
<223> OTHER INFORMATION: HIV-Vif

<400> SEQUENCE: 37

Lys Pro Pro Leu Pro Ser Val Lys Lys Leu
1               5                   10

<210> SEQ ID NO 38
<211> LENGTH: 9
<212> TYPE: PRT
<213> ORGANISM: Artificial
<220> FEATURE:
<223> OTHER INFORMATION: HIV-Vif

<400> SEQUENCE: 38
```

```
Phe Pro Arg Thr Trp Leu His Gly Leu
1               5
```

<210> SEQ ID NO 39
<211> LENGTH: 10
<212> TYPE: PRT
<213> ORGANISM: Artificial
<220> FEATURE:
<223> OTHER INFORMATION: HIVgp160

<400> SEQUENCE: 39

```
Lys Pro Cys Val Lys Leu Thr Pro Leu Cys
1               5                   10
```

<210> SEQ ID NO 40
<211> LENGTH: 9
<212> TYPE: PRT
<213> ORGANISM: Artificial
<220> FEATURE:
<223> OTHER INFORMATION: HIVgp160

<400> SEQUENCE: 40

```
Lys Val Val Ser Thr Gln Leu Leu Leu
1               5
```

<210> SEQ ID NO 41
<211> LENGTH: 10
<212> TYPE: PRT
<213> ORGANISM: Artificial
<220> FEATURE:
<223> OTHER INFORMATION: HIVgp160

<400> SEQUENCE: 41

```
Arg Pro Trp Asn Asn Thr Arg Lys Ser Ile
1               5                   10
```

<210> SEQ ID NO 42
<211> LENGTH: 9
<212> TYPE: PRT
<213> ORGANISM: Artificial
<220> FEATURE:
<223> OTHER INFORMATION: HIVgp160

<400> SEQUENCE: 42

```
Ile Pro Arg Arg Ile Arg Gln Gly Leu
1               5
```

<210> SEQ ID NO 43
<211> LENGTH: 9
<212> TYPE: PRT
<213> ORGANISM: Artificial
<220> FEATURE:
<223> OTHER INFORMATION: HIVnef

<400> SEQUENCE: 43

```
Phe Pro Val Thr Pro Gln Val Pro Leu
1               5
```

<210> SEQ ID NO 44
<211> LENGTH: 9
<212> TYPE: PRT
<213> ORGANISM: Artificial
<220> FEATURE:
<223> OTHER INFORMATION: HIVnef

<400> SEQUENCE: 44

```
Thr Pro Gln Val Pro Leu Arg Pro Met
1               5
```

<210> SEQ ID NO 45
<211> LENGTH: 10
<212> TYPE: PRT
<213> ORGANISM: Artificial
<220> FEATURE:
<223> OTHER INFORMATION: EphA2

<400> SEQUENCE: 45

Ala Pro Arg Met His Cys Ala Val Asp Leu
1               5                   10

<210> SEQ ID NO 46
<211> LENGTH: 10
<212> TYPE: PRT
<213> ORGANISM: Artificial
<220> FEATURE:
<223> OTHER INFORMATION: EphA2

<400> SEQUENCE: 46

Ala Pro Arg Val Ser Ile Arg Leu Pro Leu
1               5                   10

<210> SEQ ID NO 47
<211> LENGTH: 9
<212> TYPE: PRT
<213> ORGANISM: Artificial
<220> FEATURE:
<223> OTHER INFORMATION: Her-2/neu

<400> SEQUENCE: 47

Ala Pro Arg Glu Tyr Val Asn Ala Leu
1               5

<210> SEQ ID NO 48
<211> LENGTH: 10
<212> TYPE: PRT
<213> ORGANISM: Artificial
<220> FEATURE:
<223> OTHER INFORMATION: a HLA-B*0702 restricted peptide

<400> SEQUENCE: 48

Ala Pro Arg Gly Val Pro Gln Ile Glu Leu
1               5                   10

<210> SEQ ID NO 49
<211> LENGTH: 9
<212> TYPE: PRT
<213> ORGANISM: Artificial
<220> FEATURE:
<223> OTHER INFORMATION: MAGE-A antigen peptide

<400> SEQUENCE: 49

Ala Pro Arg Ala Leu Val Glu Thr Leu
1               5

<210> SEQ ID NO 50
<211> LENGTH: 9
<212> TYPE: PRT
<213> ORGANISM: Artificial
<220> FEATURE:
<223> OTHER INFORMATION: a HLA-B*0702 restricted peptide

<400> SEQUENCE: 50

Ala Pro Arg Met Pro Glu Ala Ala Leu
1               5

```
<210> SEQ ID NO 51
<211> LENGTH: 10
<212> TYPE: PRT
<213> ORGANISM: Artificial
<220> FEATURE:
<223> OTHER INFORMATION: TERT antigen peptide

<400> SEQUENCE: 51

Ala Pro Arg Arg Arg Leu Gly Cys Glu Leu
1               5                   10

<210> SEQ ID NO 52
<211> LENGTH: 9
<212> TYPE: PRT
<213> ORGANISM: Artificial
<220> FEATURE:
<223> OTHER INFORMATION: a HLA-B*0702 restricted peptide

<400> SEQUENCE: 52

Ala Pro Arg Pro Trp Thr Pro Cys Leu
1               5

<210> SEQ ID NO 53
<211> LENGTH: 9
<212> TYPE: PRT
<213> ORGANISM: Artificial
<220> FEATURE:
<223> OTHER INFORMATION: a HLA-B*0702 restricted peptide

<400> SEQUENCE: 53

Ala Pro Arg Ala Ser Ser Pro Leu Leu
1               5

<210> SEQ ID NO 54
<211> LENGTH: 9
<212> TYPE: PRT
<213> ORGANISM: Artificial
<220> FEATURE:
<223> OTHER INFORMATION: a HLA-B*0702 restricted peptide

<400> SEQUENCE: 54

Ala Pro Arg Gln Leu Gly Arg Glu Leu
1               5

<210> SEQ ID NO 55
<211> LENGTH: 10
<212> TYPE: PRT
<213> ORGANISM: Artificial
<220> FEATURE:
<223> OTHER INFORMATION: HSP70_115A1R3 optimized peptide

<400> SEQUENCE: 55

Ala Pro Arg Glu Ile Ser Ser Met Val Leu
1               5                   10

<210> SEQ ID NO 56
<211> LENGTH: 9
<212> TYPE: PRT
<213> ORGANISM: Artificial
<220> FEATURE:
<223> OTHER INFORMATION: HSP70_397R3L9 optimized peptide

<400> SEQUENCE: 56

Ala Pro Arg Ser Leu Gly Leu Glu Leu
1               5

<210> SEQ ID NO 57
<211> LENGTH: 9
```

```
<212> TYPE: PRT
<213> ORGANISM: Artificial
<220> FEATURE:
<223> OTHER INFORMATION: MAGE-121.1 A1R3 optimized peptide

<400> SEQUENCE: 57

Ala Pro Arg Thr Lys Ala Glu Met Leu
1               5

<210> SEQ ID NO 58
<211> LENGTH: 11
<212> TYPE: PRT
<213> ORGANISM: Artificial
<220> FEATURE:
<223> OTHER INFORMATION: HLA-B*0702-restricted cryptic eptiope
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (3)..(3)
<223> OTHER INFORMATION: Xaa is Arg or Lys or His or Met
<220> FEATURE:
<221> NAME/KEY: MISC_FEATURE
<222> LOCATION: (4)..(7)
<223> OTHER INFORMATION: Xaa are independently any naturally occurring
      amino acid
<220> FEATURE:
<221> NAME/KEY: MISC_FEATURE
<222> LOCATION: (8)..(10)
<223> OTHER INFORMATION: Xaa are independently any naturally occurring
      amino acid or none
<220> FEATURE:
<221> NAME/KEY: MISC_FEATURE
<222> LOCATION: (11)..(11)
<223> OTHER INFORMATION: Xaa is any naturally occurring amino acid with
      the proviso that if Xaa (1)..(1) is Ala then Xaa (11)..(11) is
      neither Leu nor Ala nor Ile nor Val and nor Met; and if Xaa
      (1)..(1) is not Ala then Xaa (11)..(11) is Leu or Ala or Ile or
      Val or Met

<400> SEQUENCE: 58

Xaa Pro Xaa Xaa Xaa Xaa Xaa Xaa Xaa Xaa Xaa
1               5                   10

<210> SEQ ID NO 59
<211> LENGTH: 11
<212> TYPE: PRT
<213> ORGANISM: Artificial
<220> FEATURE:
<223> OTHER INFORMATION: HLA-B*0702-restricted cryptic epitope
<220> FEATURE:
<221> NAME/KEY: MISC_FEATURE
<222> LOCATION: (1)..(1)
<223> OTHER INFORMATION: Xaa is any naturally occurring amino acid other
      than Ala
<220> FEATURE:
<221> NAME/KEY: MISC_FEATURE
<222> LOCATION: (3)..(3)
<223> OTHER INFORMATION: Xaa is Arg or Lys or His or Met
<220> FEATURE:
<221> NAME/KEY: MISC_FEATURE
<222> LOCATION: (4)..(7)
<223> OTHER INFORMATION: Xaa are independently any naturally occurring
      amino acid
<220> FEATURE:
<221> NAME/KEY: MISC_FEATURE
<222> LOCATION: (8)..(10)
<223> OTHER INFORMATION: Xaa are independently any naturally occurring
      amino acid or none
<220> FEATURE:
<221> NAME/KEY: MISC_FEATURE
<222> LOCATION: (11)..(11)
<223> OTHER INFORMATION: Xaa is Leu or Ala or Ile or Val or Met
```

```
<400> SEQUENCE: 59

Xaa Pro Xaa Xaa Xaa Xaa Xaa Xaa Xaa Xaa Xaa
1               5                   10

<210> SEQ ID NO 60
<211> LENGTH: 11
<212> TYPE: PRT
<213> ORGANISM: Artificial
<220> FEATURE:
<223> OTHER INFORMATION: HLA-B*0702-restricted cryptic epitope
<220> FEATURE:
<221> NAME/KEY: MISC_FEATURE
<222> LOCATION: (3)..(3)
<223> OTHER INFORMATION: Xaa is Arg or Lys or His or Met
<220> FEATURE:
<221> NAME/KEY: MISC_FEATURE
<222> LOCATION: (4)..(7)
<223> OTHER INFORMATION: Xaa are independently any naturally occurring
      amino acid
<220> FEATURE:
<221> NAME/KEY: MISC_FEATURE
<222> LOCATION: (8)..(10)
<223> OTHER INFORMATION: Xaa are independently any naturally occurring
      amino acid or none
<220> FEATURE:
<221> NAME/KEY: MISC_FEATURE
<222> LOCATION: (11)..(11)
<223> OTHER INFORMATION: Xaa is any naturally occurring amino acid other
      than Leu or Ala or Ile or Val or Met

<400> SEQUENCE: 60

Ala Pro Xaa Xaa Xaa Xaa Xaa Xaa Xaa Xaa Xaa
1               5                   10

<210> SEQ ID NO 61
<211> LENGTH: 11
<212> TYPE: PRT
<213> ORGANISM: Artificial
<220> FEATURE:
<223> OTHER INFORMATION: Immunogenic HLA-B*0702 restricted epitope
<220> FEATURE:
<221> NAME/KEY: MISC_FEATURE
<222> LOCATION: (3)..(3)
<223> OTHER INFORMATION: Xaa is Arg or Lys or His or Met
<220> FEATURE:
<221> NAME/KEY: MISC_FEATURE
<222> LOCATION: (4)..(7)
<223> OTHER INFORMATION: Xaa are independently any naturally occurring
      amino acid
<220> FEATURE:
<221> NAME/KEY: MISC_FEATURE
<222> LOCATION: (8)..(10)
<223> OTHER INFORMATION: Xaa are independently any naturally occurring
      amino acid or none
<220> FEATURE:
<221> NAME/KEY: MISC_FEATURE
<222> LOCATION: (11)..(11)
<223> OTHER INFORMATION: Xaa is Leu or Ala or Ile or Val or Met

<400> SEQUENCE: 61

Ala Pro Xaa Xaa Xaa Xaa Xaa Xaa Xaa Xaa Xaa
1               5                   10
```